United States Patent
Barrow et al.

(10) Patent No.: US 9,951,057 B2
(45) Date of Patent: Apr. 24, 2018

(54) COMT INHIBITING METHODS AND COMPOSITIONS

(71) Applicant: Lieber Institute for Brain Development, Baltimore, MD (US)

(72) Inventors: James Barrow, Arnold, MD (US); Glen Ernst, Bear, DE (US); Yifang Huang, Lansdale, PA (US); Ingrid Price Buchler, Baltimore, MD (US); Daniel Weinberger, Washington, DC (US)

(73) Assignee: LIEBER INSTITUTE FOR BRAIN DEVELOPMENT, Baltimore, MD (US)

( * ) Notice: Subject to any disclaimer, the term of this patent is extended or adjusted under 35 U.S.C. 154(b) by 0 days.

(21) Appl. No.: 15/011,365

(22) Filed: Jan. 29, 2016

(65) Prior Publication Data

US 2016/0222001 A1    Aug. 4, 2016

Related U.S. Application Data

(60) Provisional application No. 62/109,956, filed on Jan. 30, 2015.

(51) Int. Cl.
*A61K 31/47* (2006.01)
*C07D 417/12* (2006.01)
*C07D 215/26* (2006.01)
*C07D 405/12* (2006.01)
*C07D 401/12* (2006.01)
*A61K 31/198* (2006.01)

(52) U.S. Cl.
CPC .......... *C07D 417/12* (2013.01); *A61K 31/198* (2013.01); *C07D 215/26* (2013.01); *C07D 401/12* (2013.01); *C07D 405/12* (2013.01)

(58) Field of Classification Search
CPC .. C07D 417/12; C07D 401/12; C07D 405/12; C07D 215/26; A61K 31/198; A61K 31/47
USPC ....................................................... 514/314
See application file for complete search history.

(56) References Cited

U.S. PATENT DOCUMENTS

| | | |
|---|---|---|
| 2008/0161353 A1 | 7/2008 | Barnham et al. |
| 2010/0113529 A1 | 5/2010 | Learmonth et al. |
| 2016/0222011 A1 | 8/2016 | Barrow et al. |

FOREIGN PATENT DOCUMENTS

WO    WO 2011/114099    9/2011

OTHER PUBLICATIONS

Borchardt, "Catechol-O-Methyltransferase, 2, In Vitro Inhibition by Substituted 8-Hydroxyquinolines," J. Med. Chem., 16(4), pp. 382-387, 1973.
Pubchem-CID 14508910, Feb. 9, 2007, 10 pages.
Lieber Institute for Brain Development, Notification of Transmittal of the International Search Report and the Written Opinion of the International Searching Authority, or the Declaration for PCT/US16/15833, dated Apr. 22, 2016, 7 pages.
Ariyasu et al., "Design and Synthesis of 8-hrydroxyquinoline-based Radioprotective Agents," Bioorganic & Medicinal Chemistry, vol. 22, No. 15, pp. 3891-3905, 2014.
Cheng et al., "Solution-processible Small Molecular Organic Light-Emitting Diode Material and Devices based on the Substituted Aluminum Quinolate," Chem. Mater., vol. 16, No. 15, pp. 2862-2868, 2004.
Hafez et al., "Synthesis of Some Heterocyclic Sulfones Related to Quinolinol," Collect. Czech. Chem. Commun., vol. 58, pp. 2222-2226, 1993.
Hopkins et al., "Substituted Aluminum and Zinc Quinolates with Blue-Shifted Absorbance/luminescence Bands: Synthesis and Spectroscopic, Photoluminescence, and Electroluminescence Characterization," Chemistry of Materials, vol. 8, No. 2, pp. 344-351, 1996.
Lieber Institute for Brain Development, Supplementary European Search Report for EP 16744242.5, 8 pages, Jan. 8, 2018.

*Primary Examiner* — Taylor V Oh
(74) *Attorney, Agent, or Firm* — Kenneth H. Sonnenfeld; Bryte V. Kelly; King & Spalding LLP

(57) ABSTRACT

The present inventions include a method of inhibiting COMT enzyme in a subject as well as compounds of formula I, or a pharmaceutically acceptable salt thereof, that are useful in the treatment of various disorders mediated by COMT, including Parkinson's disease and/or schizophrenia.

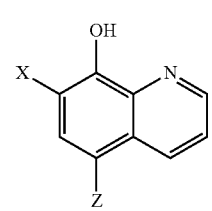

5 Claims, No Drawings

COMT INHIBITING METHODS AND COMPOSITIONS

FIELD OF THE INVENTION

This invention relates to compounds, pharmaceutical compositions and their use for treating neuropsychiatric and neurodenerative disorders. In particular, the invention relates to inhibitors of catechol-O-methyltransferase and their use as therapeutics for central nervous system disease.

BACKGROUND

Cognitive disorders are observed in many neurological and psychiatric disorders, be they neurodegenerative (e.g. Parkinson's disease, Alzheimer's disease), neurodevelopmental (e.g. schizophrenia, autism spectrum disorders) or the consequence of other etiology.

Parkinson's disease is a progressive neurodegenerative disorder (synucleopathy) diagnosed on the basis of characteristic motor disturbances, asymmetry of symptoms onset and response to levodopa (Litvan et al., 2003). Lewy bodies, neurofibrillary tangles and plaques are observed in nigral, limbic and neocortical regions. These degenerations are supposed to affect catecholaminergic (dopamine and norepinephrine) and cholinergic neurotransmission. In particular, an important part of cognitive deficits (executive function and working memory) have been related to a decreased prefrontal dopaminergic signalling in non demented patients (Nandakumar et al., 2013).

Schizophrenia is the result of a complex series of neurodevelopmental or other changes that lead to impaired information processing in the brain (Marenco and Weinberger 2000). No single genetic change, aberrant protein function, or visible brain lesion has been demonstrated to lead to schizophrenia, and many different genetic and environmental changes are linked to increased disease risk (Fatemi and Folsom 2009). While many neurochemical signaling systems, such as the various monoamines, NMDA, and GABA, are likely to play a role in the etiology of schizophrenia (Pickard 2011), many pathways seem to converge on aberrant dopamine signaling as a final common pathway that leads to many of the observed symptoms (Howes and Kapur 2009).

With regard to the cognitive impairment, for which there is currently no treatment, patients with schizophrenia show significant deficits in specific cognitive domains, especially executive function, working memory, and episodic memory. Cognitive domains which are dysfunctioning in these two disorders are complex functions involving many neurotransmitters and brain regions; however, dopamine signaling in the dorsolateral prefrontal cortex (DLPFC) has been shown to play a critical role in these processes (Goldman-Rakic, Castner et al. 2004). One approach to rectifying cortical dopamine neurotransmission is to take advantage of the differential modes of clearance of dopamine from the different brain regions. In the midbrain, there is extensive expression of the dopamine transporter (DAT), which is thought to be primarily responsible for dopamine clearance from the synapse (Ciliax, Heilman et al. 1995). In contrast, cortical regions exhibit only low levels of DAT expression, and dopamine is cleared primarily by enzymatic catabolism of dopamine, with a contribution from the norepinephrine transporter (NET) (Yavich, Forsberg et al. 2007; Kaenmaki, Tammimaki et al. 2010). The primary enzymes responsible for dopamine catabolism in the prefrontal cortex ("PFC") are monoamine oxidase (MAO) and catechol-O-methyltransferase ("COMT").

Beyond Parkinson's and schizophrenia, inhibition of COMT may be useful in a number of neuro-psychiatric conditions, including ADHD, obsessive-compulsive disorder, alcoholism, depression, bipolar disorder (Lachman, Papolos et al. 1996), as well as age-associated cognitive symptoms, impulse control disorders, including compulsive gambling, sexual behavior, and other compulsive destructive behaviors. The role of COMT in dopamine metabolism in the brain make it an especially important target for improvement of cognition (Apud and Weinberger 2007).

Additionally, COMT inhibitors have shown utility in Parkinson's disease treatment, due to the role of COMT in metabolizing the dopamine precursor L-DOPA, which is given to Parkinson's disease patients to boost the levels of dopamine in the brain (Bonifacio, Palma et al. 2007). Since dopamine cannot cross the blood-brain barrier, L-DOPA is administered in its place and is transported into the brain and subsequently processed to dopamine. The percentage of exogenously administered L-DOPA that reaches the brain is ~1%, and this low brain availability necessitates a high dose, which leads to peripheral side effects (Nutt and Fellman 1984). The primary enzymes responsible for dopamine metabolism are aromatic amino acid decarboxylase (AAAD) and COMT. Therefore, extensive efforts have been undertaken to develop potent and selective inhibitors of both enzymes. Carbidopa is an AAAD inhibitor now routinely given with L-DOPA, reducing the efficacious L-DOPA dose by 60-80% (Nutt, Woodward et al. 1985). Addition of a COMT inhibitor further decreases the variability of L-DOPA exposure, and a brain-penetrating COMT inhibitor could also increase brain dopamine levels.

Inhibitors of COMT have been developed for treatment of Parkinson's disease (Learmonth, Kiss et al. 2010). Notably, the nitrocatechol scaffold has been exploited to provide the clinically used drugs tolcapone and entacapone (Bonifacio, Palma et al. 2007). While they are effective in blocking peripheral COMT activity, entacapone has negligible brain penetration, and tolcapone has low but measurable levels in the brain (Russ, et al. 1999). Compounds with improved brain penetration should have greater efficacy for Parkinson's disease, as well as have utility for other psychiatric and neurological conditions such as cognitive impairment in schizophrenia. Despite the early clinical success achieved with tolcapone, the drug has been associated with serious liver injury, including three deaths, and requires strict liver function monitoring (Olanow and Watkins 2007). Thus, the risk-benefit profile for tolcapone prevents its widespread deployment, and new, inhibitors of COMT are needed, especially those that are active in the brain. Borchardt disclosed a series of non-nitrocatechol quinoline COMT inhibitors, but these compounds had weak potency (Borchardt, Thakker et al. 1976).

Accordingly, there remains a need for potent inhibitors of COMT and methods of using the same to treat central nervous system disorders.

SUMMARY OF THE INVENTION

The present invention provides compounds, pharmaceutical compositions and methods of treating or preventing neurological or psychiatric disorders for which inhibiting COMT provides a therapeutic effect.

The present invention also provides methods of treating or preventing a neurological or psychiatric disorder, or treating symptoms associated with a neurological or psychiatric disorder, and in particular such disorders for which inhibiting COMT provides a therapeutic effect. In a particular embodiment, the invention provides a method of inhibiting COMT enzyme in a subject by administering compounds according to formula I, or a pharmaceutically acceptable salt thereof:

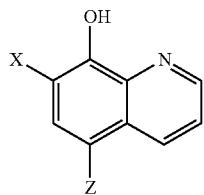

wherein:
X is selected from hydrogen, chlorine and fluorine;
Z is selected from SO$_2$R$^1$ and SO$_2$NR$^2$R$^3$;
wherein when X is hydrogen and Z is SO$_2$R$^1$, R$^1$ is selected from C$_4$ alkyl, C$_8$ alkyl, tetrahydropyran and propylcyclopropane;
when X is hydrogen and Z is SO$_2$NR$^2$R$^3$, R$^2$ and R$^3$ come together to form a 1-piperidinyl ring substituted with a α-methyl group;
when X is chlorine and Z is SO$_2$R$^1$, R$^1$ is selected from C$_3$ alkyl, C$_4$ alkyl and C$_5$-C$_6$ cycloalkyl, thiazolyl, pyridyl, pyridyl-N-oxide, and phenyl substituted with one or two groups selected from fluoro, chloro, methyl, trifluoromethyl, phenyl and tert-butyl;
when X is chlorine and Z is SO$_2$NR$^2$R$^3$, R$^2$ and R$^3$ come together to form an unsubstituted, 1-pyrrolidinyl ring;
when X is fluorine and Z is SO$_2$R$^1$, R$^1$ is selected from pyridyl, cyclopentyl, and phenyl substituted with fluoro, or trifluoromethyl, and
when X is fluorine and Z is SO$_2$NR$^2$R$^3$, R$^2$ and R$^3$ come together to form an unsubstituted, 1-pyrrolidinyl ring.

Also provided herein are COMT-inhibiting compounds in accordance with formula I, or pharmaceutically acceptable salts thereof:

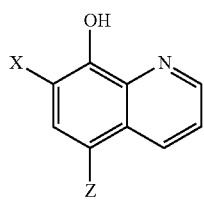

wherein:
X is selected from hydrogen, chlorine and fluorine;
Z is selected from SO$_2$R$^1$ and SO$_2$NR$^2$R$^3$;
wherein when X is hydrogen and Z is SO$_2$R$^1$, R$^1$ is selected from C$_4$ alkyl, C$_8$ alkyl, tetrahydropyran and propylcyclopropane;
when X is hydrogen and Z is SO$_2$NR$^2$R$^3$, R$^2$ and R$^3$ come together to form a 1-piperidinyl ring substituted with a α-methyl group;
when X is chlorine and Z is SO$_2$R$^1$, R$^1$ is selected from C$_3$ alkyl, C$_4$ alkyl and C$_5$-C$_6$ cycloalkyl; thiazolyl, pyridyl, pyridyl-N-oxide, and phenyl substituted with one or two groups selected from fluoro, chloro, methyl, trifluoromethyl, phenyl and tert-butyl;

when X is chlorine and Z is SO$_2$NR$^2$R$^3$, R$^2$ and R$^3$ come together to form an unsubstituted, 1-pyrrolidinyl ring;
when X is fluorine and Z is SO$_2$R$^1$, R$^1$ is selected from pyridyl, cyclopentyl and phenyl substituted with fluoro or trifluoromethyl; and
when X is fluorine and Z is SO$_2$NR$^2$R$^3$, R$^2$ and R$^3$ come together to form an unsubstituted, 1-pyrrolidinyl ring.

Also provided herein are pharmaceutical compositions comprising the COMT-inhibiting compounds of the present invention.

DETAILED DESCRIPTION OF THE INVENTION

I. Definitions

The terms below, when used herein, have the following meanings unless indicated otherwise.

As used in this specification and the appended claims, the singular forms "a", "an" and "the" include plural references unless the content clearly dictates otherwise.

When any variable (e.g. aryl, heterocycle, R$^1$, etc.) occurs more than one time in any constituent, its definition on each occurrence is independent at every other occurrence.

"Alkyl" refers to a saturated hydrocarbon chain. Such hydrocarbon chains may be branched or linear. "Alkyl" groups may be substituted by one or more substituents selected from halogen, amido, aryl or alkoxy. Particular alkyl groups according to the present invention include methyl, trifluoromethyl, ethyl, propyl, butyl, pentyl, 1-methylbutyl, 1-ethylpropyl, 3-methylpentyl, octyl and the like.

The term "C$_1$-C$_6$" (for example), or "C$_{1-6}$", includes, for this example, alkyls containing 6, 5, 4, 3, 2, or 1 carbon atom(s).

"Cycloalkyl" refers to a saturated or unsaturated cyclic hydrocarbon radical, including bridged, fused, or spiro cyclic compounds, preferably having 3 to 8 carbon atoms. Nonlimiting examples of "C$_3$-C$_6$ cycloalkyl" groups according to the present invention are cyclopropyl, cyclopentyl, cyclohexyl and the like.

The compounds of the present invention may contain one or more asymmetric centers and may thus occur as racemates, racemic mixtures, single enantiomers, diastereomeric mixtures, and individual diastereomers.

It will be understood that, as used herein, references to the compounds of the present invention are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamme, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

A "pharmaceutically acceptable excipient" or "pharmaceutically acceptable carrier" refers to an excipient that can be included in the compositions of the invention and that causes no significant adverse toxicological effects to the subject or patient to which the composition is administered. "Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The term "patient" refers to a living organism suffering from or prone to a condition that can be prevented or treated by administration of an active agent as described herein, and includes both humans and animals. In one embodiment, the patient is a human patient.

The term "mammal" "mammalian" or "mammals" includes humans, as well as animals, such as dogs, cats, horses, pigs and cattle.

Without being bound by theory, the administration of compounds according to the invention in an "effective amount" or "therapeutically effective amount" provides a concentration of the compound that functions as a COMT inhibitor sufficient to inhibit the effect of the COMT enzyme complex.

"Treating" or "treatment" of a disease state includes: 1) inhibiting the disease state, i.e., arresting the development of the disease state or its clinical symptoms; 2) attenuating the disease state, i.e. reducing the number or intensity of one or more symptoms associated with the disease state, such that one or more symptoms is reduced but may, or may not be completely eliminated; and/or 3) relieving the disease state, i.e., causing temporary or permanent regression of the disease state or its clinical symptoms.

"Prevent" or "preventing" a disease state includes: preventing the disease state, i.e. causing the clinical symptoms of the disease state not to develop in a subject that may be exposed to or predisposed to the disease state, but does not yet experience or display symptoms of the disease state.

All patents, patent applications and publications cited herein, whether supra or infra, are hereby incorporated by reference in their entirety.

II. Methods

One aspect of the invention is a method of treating or preventing a neurological or psychiatric disorder, or treating symptoms associated with a neurological or psychiatric disorder, and in particular such disorders for which inhibiting COMT provides a therapeutic effect. Without being bound by theory, the therapeutic effect provided according to the invention is achieved by inhibiting the metabolism of catecholamines by COMT. Accordingly, in an aspect of the invention, the invention provides methods of treating and/or preventing disease for which inhibiting degradation of catecholamines such as, for example, dopamine, norepinephrine or L-dihydroxyphenylalanine (L-DOPA) provides a beneficial therapeutic effect.

In another aspect, the invention provides a method of inhibiting COMT enzyme in a subject by administering compounds of formula I. These methods comprise administering to a subject in need thereof an effective amount of a COMT-inhibiting compound in accordance with formula I, or a pharmaceutically acceptable salt thereof:

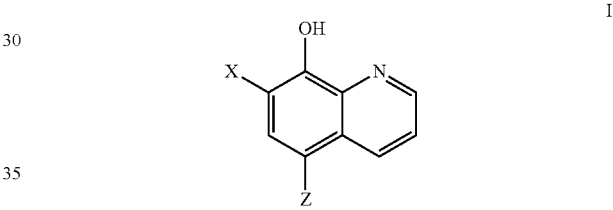

wherein:
X is selected from hydrogen, chlorine and fluorine;
Z is selected from $SO_2R^1$ and $SO_2NR^2R^3$;
wherein when X is hydrogen and Z is $SO_2R^1$, $R^1$ is selected from $C_4$ alkyl, $C_8$ alkyl, tetrahydropyran and propylcyclopropane;
when X is hydrogen and Z is $SO_2NR^2R^3$, $R^2$ and $R^3$ come together to form a 1-piperidinyl ring substituted with a α-methyl group;
when X is chlorine and Z is $SO_2R^1$, $R^1$ is selected from $C_3$ alkyl, $C_4$ alkyl and $C_5$-$C_6$ cycloalkyl, thiazolyl, pyridyl, pyridyl-N-oxide, and phenyl substituted with one or two groups selected from fluoro, chloro, methyl, trifluoromethyl, phenyl and tert-butyl;
when X is chlorine and Z is $SO_2NR^2R^3$, $R^2$ and $R^3$ come together to form an unsubstituted, 1-pyrrolidinyl ring;
when X is fluorine and Z is $SO_2R^1$, $R^1$ is selected from pyridyl, cyclopentyl and phenyl substituted with fluoro, or trifluoromethy; and
when X is fluorine and Z is $SO_2NR^2R^3$, $R^2$ and $R^3$ come together to form an unsubstituted, 1-pyrrolidinyl ring.

In a second aspect, the invention provides a method of inhibiting COMT enzyme in a subject by administering compounds according to formula I. These methods comprise administering to a subject in need thereof an effective amount of a COMT-inhibiting compound in accordance with formula I, or a pharmaceutically acceptable salt thereof:

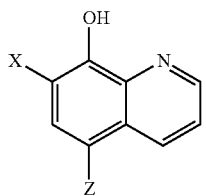

wherein:
X is hydrogen;
Z is selected from SO$_2$R$^1$ and SO$_2$NR$^2$R$^3$;
wherein when Z is SO$_2$R$^1$, R$^1$ is selected from C$_4$ alkyl, C$_8$ alkyl, tetrahydropyran and propylcyclopropane; and
when Z is SO$_2$NR$^2$R$^3$, R$^2$ and R$^3$ come together to form a 1-piperidinyl ring substituted with a α-methyl group.

In a third aspect, the invention provides a method of inhibiting COMT enzyme in a subject by administering the compounds according to formula I. These methods comprise administering to a subject in need thereof an effective amount of a COMT-inhibiting compound in accordance with formula I, or a pharmaceutically acceptable salt thereof:

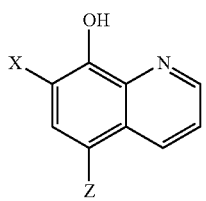

wherein:
X is chlorine;
Z is selected from SO$_2$R$^1$ and SO$_2$NR$^2$R$^3$;
wherein when Z is SO$_2$R$^1$, R$^1$ is selected from C$_3$ alkyl, C$_4$ alkyl and C$_5$-C$_6$ cycloalkyl, thiazolyl, pyridyl, pyridyl-N-oxide, and phenyl substituted with one or two groups selected from fluoro, chloro, methyl, trifluoromethyl, phenyl and tert-butyl; and
when Z is SO$_2$NR$^2$R$^3$, R$^2$ and R$^3$ come together to form an unsubstituted, 1-pyrrolidinyl ring.

In a fourth aspect, the invention provides a method of inhibiting COMT enzyme in a subject by administering the compounds according to formula I. These methods comprise administering to a subject in need thereof an effective amount of a COMT-inhibiting compound in accordance with formula I, or a pharmaceutically acceptable salt thereof:

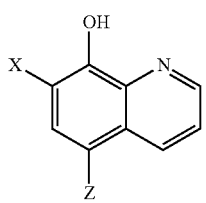

wherein:
X is fluorine;
Z is selected from SO$_2$R$^1$ and SO$_2$NR$^2$R$^3$;
wherein when Z is SO$_2$R$^1$, R$^1$ is selected from pyridyl, and phenyl substituted with fluoro, or trifluoromethyl, and when Z is SO$_2$NR$^2$R$^3$, R$^2$ and R$^3$ come together to form an unsubstituted, 1-pyrrolidinyl ring.

In a fifth aspect, the invention provides a method of inhibiting COMT enzyme in a subject by administering to a subject in need thereof an effective amount of a compound selected from the following:
5-isobutylsulfonylquinolin-8-ol;
5-octylsulfonylquinolin-8-ol;
5-tetrahydropyran-4-ylsulfonylquinolin-8-ol;
5-(3-cyclopropylpropylsulfonyl)quinolin-8-ol;
5-[(2R)-2-methylpyrrolidin-1-yl]sulfonylquinolin-8-ol;
5-[(2S)-2-methylpyrrolidin-1-yl]sulfonylquinolin-8-ol;
7-chloro-5-cyclopentylsulfonyl-quinolin-8-ol;
7-chloro-5-pyrrolidin-1-ylsulfonyl-quinolin-8-ol;
7-chloro-5-isobutylsulfonyl-quinolin-8-ol;
7-chloro-5-isopropylsulfonyl-quinolin-8-ol;
7-fluoro-5-cyclopentylsulfonyl-quinolin-8-ol;
7-chloro-5-cyclohexylsulfonyl-quinolin-8-ol;
7-chloro-5-(4-fluorophenyl)sulfonyl-quinolin-8-ol
7-fluoro-5-(4-fluorophenyl)sulfonyl-quinolin-8-ol
5-cyclopentylsulfonyl-7-fluoro-quinolin-8-ol
7-fluoro-5-[4-(trifluoromethyl)phenyl]sulfonyl-quinolin-8-ol
7-fluoro-5-(2-pyridylsulfonyl)quinolin-8-ol
7-chloro-5-(3,4-dimethylphenyl)sulfonyl-quinolin-8-ol
7-chloro-5-[4-(trifluoromethyl)phenyl]sulfonyl-quinolin-8-ol
7-chloro-5-(2-pyridylsulfonyl)quinolin-8-ol
7-chloro-5-(2,4-dimethylphenyl)sulfonyl-quinolin-8-ol
7-chloro-5-(3,5-dichlorophenyl)sulfonyl-quinolin-8-ol
7-chloro-5-thiazol-2-ylsulfonyl-quinolin-8-ol
7-chloro-5-(m-tolylsulfonyl)quinolin-8-ol
7-chloro-5-(3,4-dichlorophenyl)sulfonyl-quinolin-8-ol
7-chloro-5-(3-phenylphenyl)sulfonyl-quinolin-8-ol
5-(4-tert-butylphenyl)sulfonyl-7-chloro-quinolin-8-ol
7-chloro-5-(3-pyridylsulfonyl)quinolin-8-ol, and
7-chloro-5-(1-oxidopyridin-1-ium-3-yl)sulfonyl-quinolin-8-ol.

The compounds for use in the instant method may be selected from any one or any combination of compounds designated 1-28 herein.

For use in the method, the compound or compounds of the present invention, described above, is typically provided as a pharmaceutical composition wherein the compound or compounds is present in combination with a pharmaceutically acceptable carrier as described herein. Such pharmaceutical compositions are also provided by this disclosure.

For use in the method, the compound(s) of the present invention, described above, may also be used in combination with another additional therapeutic agent.

The methods of the present invention may be used to treat or prevent a neurological or psychiatric disorder. In particular, exemplary embodiments of the invention include methods of treating or preventing schizophrenia, major depression, a depressive phase of bipolar disorder, attention deficit disorder, attention deficit/hyperactivity disorder, sub stance dependency, or increased appetite associated with smoking cessation or antipsychotic use. Other significant indications include age-associated cognitive symptoms, impulse control disorders, including compulsive gambling, sexual behavior, and other compulsive destructive behaviors.

In addition to the psychiatric indications, the methods of the invention may also be used to treat neurological disorders. In one embodiment, the method of the present invention comprises administering an effective amount of a compound described herein above in combination with L-DOPA for treatment of Parkinson's disease. The compound can be administered in combination with L-DOPA, concurrently or separately, with or without an aromatic L-amino acid decarboxylase inhibitor (AADC) such as carbidopa, to prevent or inhibit COMT-mediated metabolism of L-DOPA.

III. Compounds

Also disclosed herein are the novel sulfonylquinolinol derivatives and novel hydroxyquinoline sulfonamide derivatives described above which, preferably, are inhibitors of catechol O-methyltransferase (COMT) enzyme, and which are useful in the treatment or prevention of neurological or psychiatric disorders or diseases in which COMT is involved. The compounds of the invention are characterized by their activity to inhibit the enzyme COMT. In preferred embodiments, the compounds of the present invention are effective to inhibit the enzyme COMT, in an assay which determines the inhibitory concentration ($IC_{50}$) for the conversion of the methyl donor S-adenosyl methionine to S-adenosyl homocysteine (SAH) as described herein, with a $pIC_{50}$ superior or equal to 4.5. In increasingly preferred embodiments, the $pIC_{50}$ as so determined is superior or equal to 6.0. In a more preferred embodiment, the $pIC_{50}$ as so determined is superior or equal to 7.0.

The ability of compounds within the scope of this invention to inhibit the activity of catechol-O-methyltransferase (COMT) may be determined by methods known to those in the art for measuring COMT inhibition. One method for measuring COMT activity uses a homogenous time-resolved fluorescent (HTRF) assay (Lina et al, 2012; kit from CisBio, Codolet, France). This assay measures the production of —S-adenosyl homocysteine (SAH) from the methyl donor S-adenosyl methionine. Using this assay preferred compounds of the invention have a $pIC_{50}$ superior or equal to 4.5. In increasingly preferred embodiments, the $pIC_{50}$ as so determined is superior or equal to 6.0. In a more preferred embodiment, the $pIC_{50}$ as so determined is superior or equal to 7.0.

Provided herein are COMT-inhibiting compounds in accordance with formula I, or pharmaceutically acceptable salts thereof:

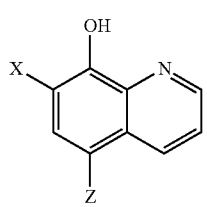

I wherein:
X is selected from hydrogen, chlorine and fluorine;
Z is selected from $SO_2R^1$ and $SO_2NR^2R^3$;
wherein when X is hydrogen and Z is $SO_2R^1$, $R^1$ is selected from $C_4$ alkyl, $C_8$ alkyl, tetrahydropyran and propylcyclopropane;
when X is hydrogen and Z is $SO_2NR^2R^3$, $R^2$ and $R^3$ come together to form a 1-piperidinyl ring substituted with a α-methyl group;
when X is chlorine and Z is $SO_2R^1$, $R^1$ is selected from $C_3$ alkyl, $C_4$ alkyl and $C_5$-$C_6$ cycloalkyl, thiazolyl, pyridyl, pyridyl-N-oxide, and phenyl substituted with one or two groups selected from fluoro, chloro, methyl, trifluoromethyl, phenyl and tert-butyl;
when X is chlorine and Z is $SO_2NR^2R^3$, $R^2$ and $R^3$ come together to form an unsubstituted, 1-pyrrolidinyl ring;
when X is fluorine and Z is $SO_2R^1$, $R^1$ is selected from pyridyl, cyclopentyl, and phenyl substituted with fluoro, or trifluoromethyl; and
when X is fluorine and Z is $SO_2NR^2R^3$, $R^2$ and $R^3$ come together to form an unsubstituted, 1-pyrrolidinyl ring.

Also provided herein are COMT-inhibiting compound in accordance with formula I, or a pharmaceutically acceptable salt thereof:

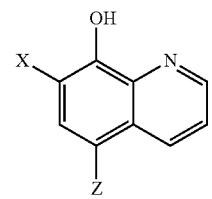

I wherein:
X is hydrogen;
Z is selected from $SO_2R^1$ and $SO_2NR^2R^3$;
wherein when Z is $SO_2R^1$, $R^1$ is selected from $C_4$ alkyl, $C_8$ alkyl, tetrahydropyran and propylcyclopropane; and
when Z is $SO_2NR^2R^3$, $R^2$ and $R^3$ come together to form a 1-piperidinyl ring substituted with a α-methyl group.

Also provided herein are COMT-inhibiting compound in accordance with formula I, or a pharmaceutically acceptable salt thereof:

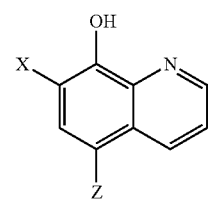

I wherein:
X is chlorine;
Z is selected from $SO_2R^1$ and $SO_2NR^2R^3$;
wherein when Z is $SO_2R^1$, $R^1$ is selected from $C_3$ alkyl, $C_4$ alkyl and $C_5$-$C_6$ cycloalkyl, thiazolyl, pyridyl, pyridyl-N-oxide, and phenyl substituted with one or two groups selected from fluoro, chloro, methyl, trifluoromethyl, phenyl and tert-butyl; and
when Z is $SO_2NR^2R^3$, $R^2$ and $R^3$ come together to form an unsubstituted, 1-pyrrolidinyl ring.

Also provided herein are COMT-inhibiting compound in accordance with formula I, or a pharmaceutically acceptable salt thereof:

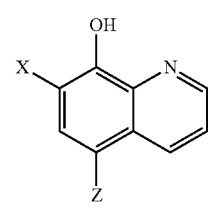

I wherein:

X is fluorine;

Z is selected from $SO_2R^1$ and $SO_2NR^2R^3$;

wherein when Z is $SO_2R^1$, $R^1$ is selected from pyridyl, cyclopentyl, and phenyl substituted with fluoro or trifluoromethyl, and when Z is $SO_2NR^2R^3$, $R^2$ and $R^3$ come together to form an unsubstituted, 1-pyrrolidinyl ring.

In particular embodiments, COMT-inhibiting compounds of the present invention are selected from the following:

5-isobutylsulfonylquinolin-8-ol;
5-octylsulfonylquinolin-8-ol;
5-tetrahydropyran-4-ylsulfonylquinolin-8-ol;
5-(3-cyclopropylpropylsulfonyl)quinolin-8-ol;
5-[(2R)-2-methylpyrrolidin-1-yl]sulfonylquinolin-8-ol;
5-[(2S)-2-methylpyrrolidin-1-yl]sulfonylquinolin-8-ol;
7-chloro-5-cyclopentylsulfonyl-quinolin-8-ol;
7-chloro-5-pyrrolidin-1-ylsulfonyl-quinolin-8-ol;
7-chloro-5-isobutylsulfonyl-quinolin-8-ol;
7-chloro-5-isopropylsulfonyl-quinolin-8-ol;
7-chloro-5-cyclohexylsulfonyl-quinolin-8-ol;
7-chloro-5-(4-fluorophenyl)sulfonyl-quinolin-8-ol;
7-fluoro-5-(4-fluorophenyl)sulfonyl-quinolin-8-ol;
7-fluoro-5-cyclopentylsulfonyl-quinolin-8-ol;
5-cyclopentylsulfonyl-7-fluoro-quinolin-8-ol;
7-fluoro-5-[4-(trifluoromethyl)phenyl]sulfonyl-quinolin-8-ol;
7-fluoro-5-(2-pyridylsulfonyl)quinolin-8-ol;
7-chloro-5-(3,4-dimethylphenyl)sulfonyl-quinolin-8-ol;
7-chloro-5-[4-(trifluoromethyl)phenyl]sulfonyl-quinolin-8-ol;
7-chloro-5-(2-pyridylsulfonyl)quinolin-8-ol;
7-chloro-5-(2,4-dimethylphenyl)sulfonyl-quinolin-8-ol;
7-chloro-5-(3, 5-dichlorophenyl)sulfonyl-quinolin-8-ol;
7-chloro-5-thiazol-2-ylsulfonyl-quinolin-8-ol;
7-chloro-5-(m-tolylsulfonyl)quinolin-8-ol;
7-chloro-5-(3,4-dichlorophenyl)sulfonyl-quinolin-8-ol;
7-chloro-5-(3-phenylphenyl)sulfonyl-quinolin-8-ol;
5-(4-tert-butylphenyl)sulfonyl-7-chloro-quinolin-8-ol;
7-chloro-5-(3-pyridylsulfonyl)quinolin-8-ol; and
7-chloro-5-(1-oxidopyridin-1-ium-3-yl)sulfonyl-quinolin-8-ol.

In some embodiments, the present invention provides prodrugs of the compounds described herein. The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated decacylated, phosphorylated or dephosphorylated to produce the active compounds.

Prodrugs may be prepared by any variety of synthetic methods or appropriate adaptations presented in the chemical literature or as in synthetic or organic chemistry text books, such as those provide in Green's Protective Groups in Organic Synthesis, Wiley, $4^{th}$ Edition (2007) Peter G. M. Wuts and Theodora W. Green; March's Advanced Organic Chemistry: Reactions, Mechanisms, and Structure, Wiley, 6th Edition (2007) Michael B. Smith and Domino Reactions in Organic Synthesis, Wiley (2006) Lutz F. Tietze, hereby incorporated by reference. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association), also hereby incorporated by reference.

Prodrugs in accordance with the invention can, for example, be produced by replacing appropriate functionalities present in the compounds disclosed herein with certain moieties known to those skilled in the art as 'pro-moieties' as described, for example, in Design of Prodrugs by H. Bundgaard (Elsevier, 1985).

Some non-limiting examples of prodrugs in accordance with the invention include: (i) where the exemplary compound contains a carboxylic acid functionality which is functionalized into a suitably metabolically labile group (esters, carbamates, etc.); (ii) where the exemplary compound contains an alcohol functionality which is functionalized into a suitably metabolically labile group (ethers, esters, carbamates, acetals, ketals, etc.); and (iii) where the exemplary compound contains a primary or secondary amino functionality, or an amide which are functionalized into a suitably metabolically labile group, e.g., a hydrolysable group (amides, carbamates, ureas, phosphonates, sulfonates, etc.). Further examples of replacement groups in accordance with the foregoing examples and examples of other prodrug types may be found in the aforementioned references.

In some embodiments, the present invention provides prodrugs of the compounds described herein. The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated decacylated, phosphorylated or dephosphorylated to produce the active compounds.

Prodrugs may be prepared by any variety of synthetic methods or appropriate adaptations presented in the chemical literature or as in synthetic or organic chemistry text books, such as those provide in Green's Protective Groups in Organic Synthesis, Wiley, $4^{th}$ Edition (2007) Peter G. M. Wuts and Theodora W. Green; March's Advanced Organic Chemistry: Reactions, Mechanisms, and Structure, Wiley, 6th Edition (2007) Michael B. Smith and Domino Reactions in Organic Synthesis, Wiley (2006) Lutz F. Tietze, hereby incorporated by reference. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association), also hereby incorporated by reference.

Prodrugs in accordance with the invention can, for example, be produced by replacing appropriate functionalities present in the compounds disclosed herein with certain moieties known to those skilled in the art as 'pro-moieties' as described, for example, in Design of Prodrugs by H. Bundgaard (Elsevier, 1985).

Some non-limiting examples of prodrugs in accordance with the invention include: (i) where the exemplary compound contains a carboxylic acid functionality which is functionalized into a suitably metabolically labile group (esters, carbamates, etc.); (ii) where the exemplary compound contains an alcohol functionality which is functionalized into a suitably metabolically labile group (ethers, esters, carbamates, acetals, ketals, etc.); and (iii) where the exemplary compound contains a primary or secondary amino functionality, or an amide which are functionalized into a suitably metabolically labile group, e.g., a hydrolysable group (amides, carbamates, ureas, phosphonates, sulfonates, etc.). Further examples of replacement groups in accordance with the foregoing examples and examples of other prodrug types may be found in the aforementioned references.

IV. Indications

As discussed above, the COMT-inhibiting compounds of the present invention can be used for treating neuropsychiatric and neurological diseases for which inhibiting COMT provides a therapeutic benefit.

Significant psychiatric indications, as discussed above, include, but are not limited to ADHD, obsessive-compulsive disorder, alcoholism and other addictions, depression, bipolar disorder, age-associated cognitive symptoms, impulse control disorders, including compulsive gambling, sexual behavior, and other compulsive destructive behaviors, in particular, schizophrenia. Among the preferred neurological diseases is treating Parkinson's disease, preferably when co-administered with L-DOPA, with or without a aromatic L-amino acid decarboxylase inhibitor (AADC) such as carbidopa, by preventing COMT-mediated metabolism of L-DOPA.

In one embodiment, a method for treating conditions in which inhibition of COMT enzyme is beneficial comprises administering to a patient in need thereof a COMT-inhibiting compound described hereinabove for use in the present methods. Such conditions include, but are not limited to, those provided in WO 2011/109254, the contents of which are incorporated herein by reference.

In a specific embodiment, a method for treating schizophrenia or psychosis comprises administering to a patient in need thereof a COMT-inhibiting compound described hereinabove for use in the present methods. The Diagnostic and Statistical Manual of Mental Disorders (DSM-IV-TR) (2000, American Psychiatric Association, Washington, D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, a method for treating cognitive disorders comprises administering to a patient in need thereof a COMT-inhibiting compound described hereinabove for use in the present methods. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), mild cognative impairment, multi-infarct dementia, Lewy body dementia, AIDS-related dementia, and Fronto temporal dementia, delirium, amnestic disorders or age related cognitive decline.

In another specific embodiment, a method for treating anxiety disorders comprises administering to a patient in need thereof a COMT-inhibiting compound described hereinabove for use in the present methods. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, a method for treating substance-related disorders and addictive behaviors comprises administering to a patient in need thereof a COMT-inhibiting compound described hereinabove for use in the present methods. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, a method for treating obesity or eating disorders associated with excessive food intake, and complications associated therewith, comprises administering to a patient in need thereof a COMT-inhibiting compound described hereinabove for use in the present methods. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, a method for treating mood and depressive disorders comprises administering to a patient in need thereof a COMT-inhibiting compound described hereinabove for use in the present methods. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, a method for treating pain comprises administering to a patient in need thereof a COMT-inhibiting compound described hereinabove for use in the present methods. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, the COMT-inhibiting compounds described hereinabove for use in the present methods can be used to treat other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with traumatic brain injury, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In particularly desirable embodiments, the COMT-inhibiting compounds, including the compounds of the present invention, are useful for treating Alzheimer's disease. Accordingly, a method for treating Alzheimer's disease comprises administering to a patient in need thereof a COMT-inhibiting compound described hereinabove for the present methods.

In other particularly desirable embodiments, the COMT-inhibiting compounds, including the compounds of the present invention, are useful for treating Parkinson's disease. Accordingly, a method for treating Parkinson's disease comprises administering to a patient in need thereof a COMT-inhibiting compound described hereinabove for the present methods.

In yet other particularly desirable embodiments, the COMT-inhibiting compounds, including the compounds of the present invention, are useful for treating mild cognitive impairment. Accordingly, a method for treating mild cognitive impairment comprises administering to a patient in need thereof a COMT-inhibiting compound described hereinabove for the present methods.

In still other particularly desirable embodiments, the COMT-inhibiting compounds, including the compounds of the present invention, are useful for treating cognitive, learning and mental related disorders in patients with neurodegeneration associated with traumatic brain injury. Accordingly, a method for treating cognitive, learning and mental related disorders in patients with neurodegeneration associated with traumatic brain injury comprises administering a COMT-inhibiting compound described hereinabove for the present methods.

In further particularly desirable embodiments, the COMT-inhibiting compounds, including the compounds of the present invention, are useful for treating schizophrenia. Accordingly, a method for treating schizophrenia comprises administering to a patient in need thereof a COMT-inhibiting compound described hereinabove for the present methods.

The subject COMT-inhibiting compounds, including the compounds of the present invention, are useful in methods for the prevention, treatment, control, amelioration, or reduction of risk of the diseases, disorders and conditions noted herein.

V. Combination Therapies

The subject COMT-inhibiting compounds, including the compounds of the present invention, are further useful in a method for the prevention or treatment of the aforementioned diseases, disorders and conditions in combination with other agents. In many instances, the combination of the drugs together is safer or more effective than either drug alone; the compounds of the present invention and the other active ingredients may often be used in lower doses than when each is used singly. The drug(s) in the combination may be administered contemporaneously or sequentially (i.e. one preceding or following the other, at any appropriate time interval). When administered contemporaneously, the drugs may be administered separately, or a single dosage form may contain both active agents.

Accordingly, the subject compounds may be used in combination with other agents which are known to be beneficial in the subject indications, or other drugs that affect receptors or enzymes that either increase the efficacy, safety, convenience, or reduce unwanted side effects or toxicity of the compounds of the present invention. It will be appreciated that any of the drugs listed herein may be in the form of a pharmaceutically acceptable salt.

In a particularly preferred embodiment, the subject compound is employed in combination with levodopa, with or without a selective extracerebral decarboxylase inhibitor such as carbidopa or benserazide. In other embodiments, the COMT inhibitor of the invention is administered in combination with anticholinergics such as biperiden and trihexyphenidyl (benzhexol) hydrochloride, other COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with a neuroleptic or antipsychotic agent, or pharmaceutically acceptable salts thereof. Classes of neuroleptic agents include phenothiazines; thioxanthenes; heterocyclic dibenzazepines; butyrophenones; diphenylbutylpiperidines; indolones, such as acepromazine, amisulpride, amoxapine, aripiprazole, asenapine, benperidol, bifeprunox, blonanserin, brexpiprazole, bromperidol, bupropion, busprione, capuride, cariprazine, carpipramine, chlorpromazine, chlorprothixene, clocapramine, clopenthixol, cloperidone, clotiapine, clozapine, cyamemazine, dexclamol, divalproex, dixyrazine, droperidol, flupentixol tiotixene, flupentixol, fluphenazine, fluphenazine, fluspirilene, haloperidol, hydroxyzine, iloperidone, levomepromazine, loxapine, lurasidone, melperone, mesoridazine, molindone, moperone, mosapramine, nefazodone, nemonapride, olanzapine, paliperidone, penfluridol, perazine, pericyazine, perlapine, perospirone, perphenazine, perphenazine, phenelzine, pimavanserin, pimozide, pipamperone, pipotiazine, prochlorperazine, promazine, promethazine, prothipendyl, quetiapine, remoxipride, risperidone, roletamide, sertindole, sulpiride, sultopride, thioproperazine, thioridazine, thiothixene, timiperone, tranylcypromaine, trazodone, trepipam, trifluoperazine, triflupromazine, trimipramine, veralipride, zicronapine, ziprasidone, zotepine, or zuclopenthixol.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, butabarbital, butalbital, capuride, carbocloral, chloral betaine, chloral hydrate, clonazepam, clorazepate, chlordiazepoxide, clorethate, cyprazepam, desipramine, dexclamol, diazepam, dichloralphenazone, divalproex, diphenhydramine, doxepin, estazolam, ethchlorvynol, etomidate, fenobam, flupentixol, fiurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nisobamate, nitrazepam, nortriptyline, oxazepam, paraldehyde, paroxetine, pentobarbital, perlapine, phenelzine, phenobarbital, prazepam, propofol, protriptyline, quazepam, reclazepam, roletamide, secobarbital, sertraline, suproclone, temazepam, tracazolate, tranylcypromaine, trazodone, triazolam, trepipam, tricetamide, triclofos, trimetozine, trimipramine, uldazepam, venlafaxine, zaleplon, zolazepam, or zolpidem.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide; venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

VI. Formulation and Administration

The invention provides a method for administering a COMT inhibiting compound as provided herein to a patient suffering from a condition, or prone to a condition, that is responsive to treatment or prevention with the compound. The method comprises administering, e.g. orally or parenterally, a therapeutically effective amount of the compound, preferably provided as part of a pharmaceutical preparation.

The invention also provides pharmaceutical preparations comprising a COMT-inhibiting compound as provided herein in combination with a pharmaceutical excipient.

Modes of administration include administration by injection, e.g. parenteral, intravenous, intraarterial, intramuscular, subcutaneous, and intrathecal, as well as pulmonary, rectal, transdermal, transmucosal, and oral delivery.

In addition to primates, such as humans, a variety of other mammals can be treated according to the method of the present invention. For instance, mammals including, but not limited to, cows, sheep, goats, horses, dogs, cats, guinea pigs, or other bovine, ovine, equine, canine, feline, or rodent, such as mouse, species can be treated. However, the method can also be practiced in other species, such as avian species (e.g., chickens).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Suitable formulation types for parenteral administration include ready-for-injection solutions, dry powders for combination with a solvent prior to use, suspensions ready for injection, dry insoluble compositions for combination with a vehicle prior to use, emulsions and liquid concentrates for dilution prior to administration.

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include, but are not limited to, water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and *arachis* oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

Exemplary excipients include, without limitation, carbohydrates, inorganic salts, antimicrobial agents, antioxidants, surfactants, buffers, acids, bases, and combinations thereof. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer including, but not limited to, citric acid, sodium chloride, potassium chloride, sodium sulfate, potassium nitrate, sodium phosphate monobasic, sodium phosphate dibasic, and combinations thereof.

A surfactant may be present as an excipient. Exemplary surfactants include, but are not limited to, polysorbates such as Tween 20 and Tween 80 and pluronics such as F68 and F88 (both available from BASF, Mount Olive, N.J.); sorbitan esters; lipids, such as phospholipids such as lecithin and other phosphatidyl cholines, phosphatidyl ethanolamines (although preferably not in liposomal form), and fatty acids and fatty esters.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

For pressurized compositions, the liquid carrier can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The compositions may be administered topically, as a solution, cream, or lotion, by formulation with pharmaceutically acceptable vehicles containing the active compound. The compositions can be in a form suitable for use in transdermal devices.

The compositions of this invention may be orally administered, in formulations such as capsules, tablets, powders or granules, or as suspensions or solutions in water or non-aqueous media. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

The amount of the compound in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the COMT-inhibiting compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then further exploring the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

The foregoing pharmaceutical excipients, along with other excipients, are described in "Remington: The Science & Practice of Pharmacy", 21st ed., Williams & Williams, (2005), the "Physician's Desk Reference", 67th ed., PDR Network, Montvale, N.J. (2013), and Kibbe, A. H., "Handbook of Pharmaceutical Excipients", 7th Edition, Pharmaceutical Press, Washington, D.C., 2012.

The dose of the compounds according to the invention to be administered, both unit dosage and dosing schedule, will vary depend upon the age, weight, and general condition of the subject, as well as the desired therapeutic effect, the route of administration, and the duration of the treatment. The compounds of the invention are administered to the patient in therapeutically effective amounts. Methods are known to those skilled in the art to adjust the dose to obtain maximal benefit. Generally, dosage levels of between 0.001 to 10 mg/kg of body weight daily are administered to the patient. The dosage range will generally be about 0.5 mg to 1.0 g per patient per day, which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. The compounds may be administered on a regimen of 1 to 4 times per day, such as once or twice per day.

These and other aspects of the invention will be realized upon closer inspection of the specification as a whole.

EXAMPLES

The present compounds can be prepared and evaluated according to procedures provided in the following Examples. The following Examples further describe, but do not limit, the scope of the invention.

COMT Inhibition Assay Procedure

The ability of compounds to inhibit the activity of catechol-O-methyltransferase (COMT) was determined by a homogenous time-resolved fluorescent (HTRF) assay (Lina et al, 2012; kit from CisBio, Codolet, France). This assay measures the production of S-adenosyl homocysteine (SAH) from the methyl donor S-adenosyl methionine. Recombinant human membrane bound COMT (MB-COMT; M51A variant) was expressed in HEK 293F cells using 293Fectin (Life Technologies, Gent, Belgium) and membranes prepared. The membranes were re-suspended in buffer (20 mM Tris/HCl pH 7; 10 mM glycerol; 2 mM $MgCl_2$; 10 mM NaCl), aliquoted and stored at −80° C. Recombinant human soluble COMT (S-COMT), Val158 variant and a hexa-His tag on the N-terminus, was purified using Ni-NTA chromatography, the His tag removed and stored in buffer as above.

For the human MB-COMT assay, membranes (62 ng/well) were incubated with SAM (20 µM final, CisBio) and dopamine (1.5 µM final; Sigma H8502, Diegem, Belgium) in the presence or absence of varying concentrations (typically 10 concentrations ranging from 10 µM to 0.1 nM) of compound for 40 min at 37° C. in 384-well microtitre plates (10 µl per well final volume). The reaction was terminated by the addition of acylation buffer and the amount of SAH produced determined according to manufacturer's instructions. Specific inhibition as that inhibited by a high concentration of tolcapone (10 µM; synthesised at UCB) and all experiments were validated using a control curve to tolcapone.

The human S-COMT assay was performed as above except that 0.15 ng enzyme/well was incubated with SAM (20 µM final) and dopamine (100 µM final) for 15 min at 37° C. and SAH production determined.

HTRF readings were performed using a Perkin Elmer Envision and results expressed as concentration of SAH produced using a standard curve. Results were analysed using non-linear regression to the 4-parameter logistic equation and pIC50 (−log 10 concentration of drug which inhibits enzyme activity/SAH production by 50%) determined.

As the data herein indicate, a broad variety of compounds of formula I were found effective as COMT inhibitors at low concentrations. $pIC_{50}$ values for exemplary compounds of formula I (see below for compound names and structures) are provided in Table 1 below. Any compound with a $pIC_{50}$ superior or equal to 4.5 in this assay, as described above, is deemed a COMT inhibitor. In the Table 1 below, a single plus (+) is associated with a $pIC_{50}$ of from about 4.5 to 6; two plus signs (++) is associated with a $pIC_{50}$ of from about great than 6 to 7; and three plus signs (+++) is associated with a $pIC_{50}$ of above about 7.

TABLE 1

| Example | Activity range |
|---------|----------------|
| 1  | +++ |
| 2  | +++ |
| 3  | ++  |
| 4  | +++ |
| 5  | +++ |
| 6  | +++ |
| 7  | ++  |
| 8  | ++  |
| 9  | ++  |
| 10 | +++ |
| 11 | +   |
| 12 | ++  |
| 13 | +++ |
| 14 | ++  |
| 15 | ++  |
| 16 | ++  |
| 17 | ++  |
| 18 | ++  |
| 19 | ++  |
| 20 | +++ |
| 21 | +   |
| 22 | ++  |
| 23 | ++  |
| 24 | ++  |
| 25 | ++  |
| 26 | +   |
| 27 | +   |
| 28 | +   |

Synthetic Procedures

Exemplary compounds were prepared via several general synthetic routes set forth in the Examples below. Any of the disclosed compounds of the present invention can be prepared according to one or more of these synthetic routes or specific examples, or via modifications thereof accessible to the person of ordinary skill in the art.

Method A: 5-isobutylsulfonylquinolin-8-ol

Example 1

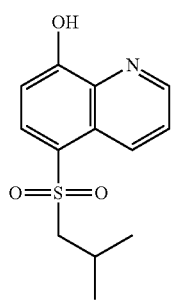 [SMILES: CC(C)CS(=O)(=O)c1ccc(O)c2ncccc12]

Step 1: 8-benzyloxy-5-isobutylsulfanyl-quinoline

To a stirring solution of 8-benzyloxyquinoline-5-sulfonyl chloride (142 mg, 0.3 mmol) in THF (3 mL) with stirring, triphenylphosphine (235 mg, 0.90 mmol) was added. The solution was heated at 60° C. for 30 min. The solution was cooled to room temperature. Diethyl ether (5 mL) was added. The precipitate was isolated by filtration and dried, then dissolved in DMF (3 ml) and sodium borohydride (15 mg, 0.39 mmol) was added. The solution was stirred at room temperature 30 min. Sodium hydride (14 mg, 60%, 0.6 mmol) was added followed by 1-iodo-2-methylpropane (83 mg, 0.45 mmol). The solution was heated to 60° C. for 2 hrs then cooled to room temperature and quenched with water (4 ml) and extracted with ethyl acetate (3×5 ml). The combined organic extract was washed with water (3×4 ml), brine (5 ml), dried over sodium sulfate, filtered and concentrated. The residue was purified by automated flash chromatography (0-50% EtOAc/hexanes, 4 g silica gel cartridge) to give the title compound as a colorless oil (50 mg). MS (ES+) m/z 324.0 $[M+H]^+$. $^1$H NMR (400 MHz, chloroform-d) δ ppm 9.02 (dd, J=4.0, 1.8 Hz, 1H), 8.79-8.85 (m, 1H), 7.58-7.61 (m, 1H), 7.51-7.57 (m, 3H), 7.36-7.42 (m, 2H), 7.30-7.35 (m, 1H), 6.95-7.01 (m, 1H), 5.47 (s, 2H), 2.66-2.74 (m, 2H), 1.66-1.83 (m, 1H), 0.98-1.04 (m, 6H).

Step 2: 8-benzyloxy-5-isobutylsulfonyl-quinoline

To a stirring solution of 8-benzyloxy-5-isobutylsulfanyl-quinoline (46 mg, 0.14 mmol) in dichloromethane (1 mL), mCPBA (70 mg, 0.28 mmol) was added. The solution was stirred at room temperature for 30 min, then 2 ml dichloromethane was added followed by 1 ml 10% sodium bisulfite. The mixture was washed with aqueous sodium hydroxide (1N, 2 ml), water (2 ml), and brine (2 ml), dried over sodium sulfate, filtered and concentrated. The residue was purified by automated flash chromatography (0-50% EtOAc/hexanes, 4 g silica gel cartridge) to give the title compound as white solid (35 mg). MS (ES+) m/z 356.1 $[M+H]^+$. $^1$H NMR (400 MHz, chloroform-d) δ ppm 9.02 (dd, J=4.0, 1.5 Hz, 1H), 8.96 (dd, J=8.8, 1.5 Hz, 1H), 8.23 (d, J=8.6 Hz, 1H), 7.81 (dd, J=8.8, 4.0 Hz, 1H), 7.58 (d, J=7.8 Hz, 2H), 7.36-7.53 (m, 3H), 5.43 (s, 2H), 3.39 (br. s., 2H), 3.30 (d, J=6.6 Hz, 2H), 1.98-2.12 (m, 1H), 0.95 (d, J=6.8 Hz, 6H).

Step 3: 5-isobutylsulfonylquinolin-8-ol

To a stirring solution of 8-benzyloxy-5-isobutylsulfonyl-quinoline (32 mg, 0.09 mmol) in acetic acid (0.2 ml), hydrobromic acid (48%, 0.6 mL) was added. The solution was stirred at 100° C. for 16 hrs. The solution was cooled to room temperature. The solution was diluted with diethyl ether. The precipitate was collected by filtration and dried to give the title compound as a HBr salt, a white solid (14 mg). MS (ES+) m/z 266.0 $[M+H]^+$. $^1$H NMR (400 MHz, DMSO-d6) δ ppm 8.98-9.10 (m, 2H), 8.13-8.21 (m, 1H), 7.87 (dd, J=8.7, 4.4 Hz, 1H), 7.22-7.30 (m, 1H), 3.22-3.32 (m, 2H), 1.99-2.10 (m, 1H), 0.87-0.98 (m, 7H)

The following compounds were prepared using the method above:

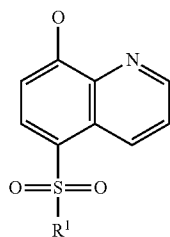

| Example | Name | R¹ | Data | Preparation Information |
|---|---|---|---|---|
| 2 | 5-octylsulfonylquinolin-8-ol | | MS (ES+) m/z 322.0 [M + H]⁺. ¹H NMR (400 MHz, DMSO-d6) δ ppm: 9.00-9.09 (m, 2H), 8.14 (d, J = 8.3 Hz, 1H), 7.81-7.90 (m, 1H), 7.27 (d, J = 8.3 Hz, 1H), 3.29-3.41 (m, 2H), 1.43-1.58 (m, 2H), 1.06-1.28 (m, 7H), 0.75-0.86 (m, 3H) | A, Using 1-bromooctane |
| 3 | 5-tetrahydropyran-4-ylsulfonyquinolin-8-ol | | MS (ES+) m/z 294.0 [M + H]⁺. ¹H NMR (400 MHz, DMSO-d6) δ ppm: 8.99-9.09 (m, 2H), 8.06-8.16 (m, 1H), 7.76-7.87 (m, 1H), 7.23-7.31 (m, 1H), 3.87 (dd, J = 10.5, 3.7 Hz, 2H), 3.50-3.62 (m, 1H), 3.13-3.31 (m, 3H), 1.53-1.76 (m, 4H) | A, Using 4-iodotetrahydrofuran |
| 4 | 5-(3-cyclopropylpropylsulfonyl)quinolin-8-ol | | MS (ES+) m/z 291.0 [M + H]⁺. ¹H NMR (400 MHz, DMSO-d6) δ ppm: 9.02-9.14 (m, 2H), 8.19 (d, J = 8.3 Hz, 1H), 7.89 (dd, J = 8.7, 4.4 Hz, 1H), 7.29 (d, J = 8.3 Hz, 1H), 3.43 (d, J = 6.8 Hz, 2H), 2.01-2.16 (m, 1H), 1.62-1.75 (m, 2H), 1.33-1.56 (m, 4H), 1.05-1.21 (m, 2H) | A, Using 3-cyclopropyl-1-iodopropane |

Method B: 5-[(2R)-2-methylpyrrolidin-1-yl]sulfonylquinolin-8-ol

Example 5

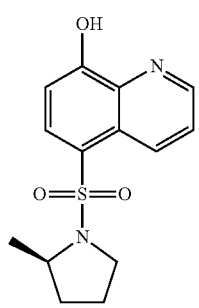 [SMILES: C[C@@H]1CCCN1S(=O)(=O)c1ccc(O)c2ncccc12]

Step 1: 8-fluoroquinoline-5-sulfonyl chloride 8-fluoroquinoline (2.24 g, 15.22 mmol) was added dropwise with stirring to chlorosulfonic acid (10 mL, 150.45 mmol). The resulting mixture was stirred at 100° C. for 16 h, 125° C. for 6 h, then 100° C. for 26 h. The reaction mixture was carefully added dropwise to ice-water with stirring. The solid was collected by filtration and air-dried to give 8-fluoroquinoline-5-sulfonyl chloride (2.61 g, 70% yield) as a white solid. MS (ES+) m/z 246.0 [M+H]⁺. ¹H NMR (400 MHz, DMSO-d6) δ ppm 9.36 (d, J=8.59 Hz, 1H), 9.04 (d, J=3.28 Hz, 1H), 8.02 (dd, J=8.08, 5.31 Hz, 1H), 7.82 (dd, J=8.72, 4.42 Hz, 1H), 7.62 (dd, J=10.61, 8.08 Hz, 1H).

Step 2: trimethyl-[2-[[5-[(2R)-2-methylpyrrolidin-1-yl]sulfonyl-8-quinolyl]oxy]ethyl]silane 8-fluoroquinoline-5-sulfonyl chloride (150 mg, 0.61 mmol) was suspended in THF (3 mL). To this suspension was added diisopropylethylamine (220 μL, 1.26 mmol), followed by 2(R)-2-methylpyrrolidine (0.06 ml, 0.62 mmol). The resulting mixture was stirred at room temperature for 15 min. A suspension of 2-(trimethylsilyl)ethanol (0.446 mL, 3.11 mmol) and 60% sodium hydride (125 mg, 3.1 mmol) in THF (2 mL) were added and the resulting mixture was stirred at ambient temperature for 30 min. Water was added and the mixture extracted with CHCl₃. The organic layer was concentrated in vacuo, and the residue purified by automated normal-phase chromatography (0-100% EtOAc/hexanes, 4 g silica gel cartridge) to give the title compound (160 mg) as a colorless solid. MS (ES+) m/z 393.0 [M+H]⁺. ¹H NMR (400 MHz, DMSO-d6) δ ppm −0.06-0.18 (m, 9H), 1.12 (d, J=6.32 Hz, 3H), 1.17-1.32 (m, 2H), 1.35-1.62 (m, 2H), 1.75 (dd, J=13.01, 7.45 Hz, 2H), 3.06-3.31 (m, 2H), 3.67-3.87 (m, 1H), 4.24-4.43 (m, 2H), 7.35 (d, J=8.59 Hz, 1H), 7.75 (dd, J=8.84, 4.04 Hz, 1H), 8.16 (d, J=8.34 Hz, 1H), 8.84-9.11 (m, 2H).

Step 3: 5-[(2R)-2-methylpyrrolidin-1-yl]sulfonylquinolin-8-ol

To a solution of trimethyl-[2-[[5-[(2R)-2-methylpyrrolidin-1-yl]sulfonyl-8-quinolyl]oxy]ethyl]silane (157. mg, 0.4000 mmol) in DMF (2 mL) was added cesium fluoride (182.2 4 mg, 1.2 mmol). The contents were stirred at 60° C. for 3 hours. Ethyl acetate was added and the mixture washed with water (3×), brine, dried with magnesium sulfate, filtered and the solvent removed in vacuo. The residue was partitioned between dichloromethane and water, and the organic extract was dried over magnesium sulfate, filtered and concentrated to give 64 mg of a solid. MS (ES+) m/z 293.0 [M+H]+. 1H NMR (400 MHz, DMSO-d6) δ ppm 9.03 (dd, J=8.72, 1.14 Hz, 1H), 8.95 (dd, J=4.04, 1.26 Hz, 1H), 8.08 (d, J=8.59 Hz, 1H), 7.13 (d, J=8.34 Hz, 1H), 7.76 (dd, J=8.97, 4.17 Hz, 1H), 3.77 (td, J=6.51, 3.92 Hz, 1H), 3.21-3.29 (m, 1H), 3.11-3.20 (m, 1H), 1.65-1.86 (m, 2H), 1.54 (dt, J=11.87, 5.05 Hz, 1H), 1.39-1.49 (m, 1H), 1.11 (d, J=6.32 Hz, 3H).

The following compounds were prepared using the method above:

Step 1: 8-fluoroquinoline-5-sulfonyl chloride

8-Fluoroquinoline (2.5 g, 16.99 mmol) was added dropwise with stirring to chlorosulfonic acid (7.04 mL, 105.95 mmol). The resulting mixture was stirred at 110° C. for 18 h. The reaction mixture was added dropwise to ice-water with stirring. The solid was collected by filtration and air-dried to give the product as a beige solid (903 mg, 21.7% yield). MS (ES+) m/z 246.0 [M+H]+. 1H NMR (400 MHz, DMSO-d6) δ ppm: 7.56 (dd, J=10.86, 8.08 Hz, 3H), 7.74 (dd, J=8.72, 4.17 Hz, 3H), 7.98 (dd, J=8.08, 5.31 Hz, 3H), 8.99 (dd, J=4.17, 1.64 Hz, 3H), 9.27 (dt, J=8.72, 1.71 Hz, 3H).

Step 2: trimethyl-[2-[(5-pyrrolidin-1-ylsulfonyl-8-quinolyl)oxy]ethyl]silane To a suspension of 8-fluoroquinoline-5-sulfonyl chloride (2.0 g, 8.1 mmol) in THF (25 mL) was added DIPEA (2.8 mL, 16.2 mmol) at ambient temperature. Pyrrolidine (0.67 mL, 8.1 mmol) was added slowly dropwise as a solution in THF (5 ml). Meanwhile to a slurry of sodium hydride (976.9 mg, 24.4 mmol) in THF (15 ml) was added 2-(trimtheylsilyl) ethanol (3.5 mL, 24.4 mmol). After complete addition of pyrrolidine to the 8-fluoroquinoline-5-sulfonyl chloride, HPLC confirmed the sulfonamide formation was complete. This sulfonamide mixture was added to the slurry of trimethylsilylethanol sodium salt slowly to limit exotherm. The

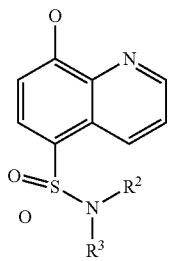

| Ex. | —NR²R³ | Name | Data | Prep Info |
|---|---|---|---|---|
| 6 | (pyrrolidine with methyl, wedge) | 5-1(2S)-2-methylpyrrolidin-1-yl]sulfonylquinolin-8-ol | MS (ES+) m/z 293.0 [M + H]+ 1H NMR (400 MHz, DMSO-d6) δ ppm 11.02 (br. s., 1H) 9.05 (dd, J = 8.84, 1.52 Hz, 1H) 8.98 (dd, J = 4.04, 1.52 Hz, 1H) 8.11 (d, J = 8.34 Hz, 1H) 7.78 (dd, J = 8.84, 4.04 Hz, 1H) 7.19 (d, J = 8.34 Hz, 1H) 3.78 (td, J = 6.69, 4.04 Hz, 1H) 3.23-3.32 (m, 1H) 3.11-3.21 (m, 1H) 1.66-1.86 (m, 2H) 1.49-1.60 (m, 1H) 1.40-1.49 (m, 1H) 1.12 (d, J = 6.32 Hz, 3H) | B |

Method C:
7-chloro-5-pyrrolidin-1-ylsulfonyl-quinolin-8-ol

Example 7

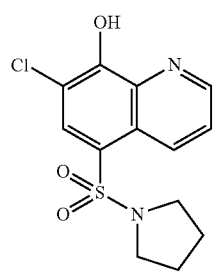 [SMILES: O=S(=O)(c1cc(Cl)c(O)c2ncccc12)N1CCCC1]

reaction was allowed to stir at ambient temperature for one hour prior to quenching by addition of water. Ethyl acetate was added and the layers were separated. The aqueous layer was extracted (3×50 ml) with ethyl acetate. The organics were combined, dried over sodium sulfate, concentrated to a residue and purified by silica chromatography (100 g) eluting 0-100% ethyl acetate/hexanes to yield 2.15 g, 70% of a white powder. MS (ES+) m/z 379.0 [M+H]+. 1H NMR (400 MHz, DMSO-d6) δ ppm 0.13 (s, 9H), 1.15-1.33 (m, 2H), 1.59-1.79 (m, 4H), 3.06-3.24 (m, 4H), 4.21-4.47 (m, 2H), 7.35 (d, J=8.59 Hz, 1H), 7.75 (dd, J=8.84, 4.04 Hz, 1H), 8.14 (d, J=8.59 Hz, 1H), 8.88-9.08 (m, 2H).

Step 3: 5-pyrrolidin-1-ylsulfonylquinolin-8-ol

To a solution of trimethyl-[2-[(5-pyrrolidin-1-ylsulfonyl-8-quinolyl)oxy]ethyl]silane (2.15 g, 5.6 mmol) dissolved in THF (35 mL) was added tetrabutylammonium fluoride (5.6 mL, 5.6 mmol) as a 1M solution in THF. The mixture was allowed to stir for 1 hour. Excess solvent was removed by rotary evaporator and resultant residue partitioned between water and ethyl acetate. After 2 extractions with ethyl acetate, this solvent proved to be poor in removing the desired product into the organic layer. Extraction of the aqueous material was accomplished by (3×30 ml) dichloromethane. The organic layer was dried over sodium sulfate and concentrated to an oil. The material was purified by silica chromatography eluting 0-10% dichloromethane/methanol to yield (548 mg, 34%) a white solid. MS (ES+) m/z 279.0 [M+H]+. 1H NMR (400 MHz, DMSO-d6) δ ppm 1.71 (dt, J=6.51, 3.44 Hz, 4H), 3.07-3.23 (m, 4H), 7.20 (d, J=8.34 Hz, 1H), 7.78 (dd, J=8.84, 4.29 Hz, 1H), 8.09 (d, J=8.34 Hz, 1H), 8.98 (dd, J=3.79, 1.26 Hz, 1H), 9.04 (dd, J=8.72, 1.64 Hz, 1H), 11.02 (br. s., 1H).

Step 4:
7-chloro-5-pyrrolidin-1-ylsulfonyl-quinolin-8-ol

A solution of 5-pyrrolidin-1-ium-1-ylsulfonylquinolin-8-ol; 2,2,2-trifluoroacetate (50 mg, 0.13 mmol) suspended in chloroform (2.5 mL) was added N,N-diisopropylethylamine (0.06 mL, 0.32 mmol). When the mixture became a homogeneous solution, N-chlorosuccinimide (25.5 mg, 0.19 mmol) was added at ambient temperature. The reaction was heated to 40° C. After one hour additional NCS was added and the material stirred at 40° C. overnight. The reaction was cooled to ambient temperature and extracted (3×2 ml) 10% sodium thiosulfate. The organic layer was passed through a phase separator tube and concentrated to a solid. The solid was suspended in methanol and DMF with 4 drops of 1N HCl. The insoluble materials were collected by filtration to yield orange solids (14.9 mg, 37% yield). MS (ES+) m/z 313.0 [M+H]+. 1H NMR (400 MHz, CDCl3) δ ppm 1.86 (s, 4H), 3.33 (s, 4H), 7.61-7.68 (m, 1H), 8.27 (s, 1H), 8.88-8.94 (m, 1H), 9.12-9.20 (m, 1H).

Method D:
7-chloro-5-cyclopentylsulfonyl-quinolin-8-ol

Example 8

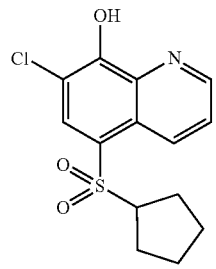 [SMILES: O=S(=O)(c1cc(Cl)c(O)c2ncccc12)C1CCCC1]

Step 1: 5-bromo-7-chloro-quinolin-8-ol

To a solution of 5-bromoquinolin-8-ol (3.01 g, 13.43 mmol) in chloroform (50 mL) was added N-chlorosuccinimide (1.97 g, 14.78 mmol) in one portion. The resulting suspension was stirred at ambient temperature for 3 h, stirred at 40° C. for 19 h, then at 60° C. for 23 h. The solvent was removed in vacuo to give a dark green solid. This material was triturated with MeOH, collected by filtration and air-dried to give 5-bromo-7-chloro-quinolin-8-ol (2.49 g, 9.63 mmol, 71.7% yield) as a green solid. 1H NMR (400 MHz, DMSO-d6) δ ppm: 11.08 (br. s, 1H), 8.99 (br. s, 1H), 8.47 (d, J=6.32 Hz, 1H), 7.99 (br. s, 1H), 7.77 (br. s, 1H).

Step 2: 8-benzyloxy-5-bromo-7-chloro-quinoline

To a solution of 5-bromo-7-chloro-quinolin-8-ol (9 g, 34.82 mmol) in acetonitrile (100 mL) with stirring, benzyl bromide (4.55 mL, 38.3 mmol) was added. The solution was stirred at 50° C. for 7 hours. The solution was cooled to room temperature. The solution was filtered. Water (50 mL) was added. The off-white precipitate (crystals) was collected by filtration. The off white solid was washed with water and air-dried to give 8-benzyloxy-5-bromo-7-chloro-quinoline (9.27 g, 26.59 mmol, 76.4% yield) as off white solid. MS (ES+) m/z 349.0 [M+H]+. 1H NMR (400 MHz, DMSO-d6) δ ppm: 8.99-9.04 (m, 1H), 8.48-8.53 (m, 1H), 7.83-7.87 (m, 1H), 7.59-7.67 (m, 2H), 7.52-7.58 (m, 1H), 7.32-7.43 (m, 3H), 5.47-5.51 (m, 2H).

Step 3: 8-benzyloxy-7-chloro-5-cyclopentylsulfanyl-quinoline

To a stirring solution of 8-benzyloxy-5-bromo-7-chloro-quinoline (7.6 g, 21.8 mmol) in dioxane (100 mL), cyclopentanethiol (3.5 mL, 32.7 mmol), tris(dba)dipalladium (1 g, 1.09 mmol), xantphos (0.52 g, 1.09 mmol), cesium carbonate (21.31 g, 65.4 mmol) were added. Nitrogen was bubbled in for 3 min. The solution was heated at 90° C. for overnight. The reaction was not complete. Another portion of catalysts and cyclopentanethiol (3.5 mL, 32.7 mmol) were added. The reaction was continued 6 hours at 90° C. Water (150 mL) was added. The solution was extracted with ethyl acetate (2×100 mL), brine (50 ml), and dried over sodium sulfate. The organic solution was filtered and concentrated. The residue was purified over ISCO eluted with ethyl acetate/hexane (0-30%) to give 8-benzyloxy-7-chloro-5-cyclopentylsulfanyl-quinoline (7.55 g, 20.41 mmol, 93.6% yield) as a slightly colored oil. 1H NMR (chloroform-d6) δ ppm: 9.01 (dd, J=4.2, 1.6 Hz, 1H), 8.71-8.80 (m, 1H), 7.66-7.69 (m, 1H), 7.60-7.66 (m, 2H), 7.46-7.54 (m, 1H), 7.31-7.44 (m, 3H), 5.45-5.52 (m, 2H), 3.52-3.63 (m, 1H), 1.96-2.10 (m, 2H), 1.76-1.91 (m, 2H), 1.56-1.72 (m, 4H).

Step 4: 8-benzyloxy-7-chloro-5-cyclopentylsulfonyl-quinoline

To a stirring solution of 8-benzyloxy-7-chloro-5-cyclopentylsulfanyl-quinoline (7.55 g, 20.41 mmol) in DCM (100 mL) at 0° C., and 3-chlorobenzenecarboperoxoic acid (10.06 mL, 40.82 mmol) was added slowly into the solution. The reaction was continued at 0° C. for 20 min. and room temperature 20 min. Sodium sulfite (1.0 N solution, 30 mL) was added. Sodium hydroxide solution (1.0 N, 100 mL) was added. The solution was stirred at room temperature for 20 min. DCM (100 mL) was added. The aqueous phase was removed. The solution was extracted with sodium hydroxide solution (1.0 N, 50 mL), water (100 mL), brine (100 mL) and dried over sodium sulfate. The solution was filtered and concentrated. The residue was purified by automated normal-phase chromatography, eluting with ethyl acetate/hexane (0-60%) to give 8-benzyloxy-7-chloro-5-cyclopentylsulfonyl-quinoline (6.9 g, 17.17 mmol, 84.1% yield) as a white solid. 1H NMR (chloroform-d6) δ ppm: 9.06-9.18 (m, 2H), 8.35 (s, 1H), 7.54-7.67 (m, 3H), 7.32-7.43 (m, 3H), 5.69 (s, 2H), 3.56-3.68 (m, 1H), 2.06-2.19 (m, 2H), 1.77-1.91 (m, 4H), 1.60-1.71 (m, 2H).

Step 5: 7-chloro-5-cyclopentylsulfonyl-quinolin-8-ol 8-benzyloxy-7-chloro-5-cyclopentylsulfonyl-quinoline (6.9 g, 17.17 mmol) in hydrochloric acid (81.6 mL, 489.46 mmol) was stirred at 100° C. for two hours. The solution was cooled in ice-water bath for 30 min. The yellow precipitate was isolated by filtration and washed with diethyl ether and air-dried to give 7-chloro-5-cyclopentylsulfonyl-quinolin-8-ol (5.26 g, 16.871 mmol, 98.3% yield) as a yellow solid. $^1$H NMR (DMSO-d6) δ ppm: 8.99-9.11 (m, 2H), 8.14 (s, 1H), 7.85 (dd, J=8.6, 4.0 Hz, 1H), 3.82-3.93 (m, 1H), 1.82-1.94 (m, 2H), 1.62-1.82 (m, 4H), 1.49-1.61 (m, 2H).

Method E:
7-chloro-5-(4-fluorophenyl)sulfonyl-quinolin-8-ol

Example 9

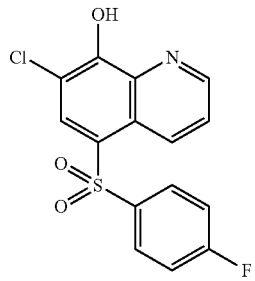 [SMILES: O=S(=O)(c1ccc(F)cc1)c1cc(Cl)c(O)c2ncccc12]

Step 1: 2-[(8-benzyloxy-7-chloro-5-quinolyl)sulfanyl]ethyl-trimethyl-silane

To a stirring solution of 8-benzyloxy-5-bromo-7-chloro-quinoline (5.9 g, 16.92 mmol) in dioxane (100 mL), 2-trimethylsilylethanethiol (3.57 mL, 25.39 mmol) tris(dba)dipalladium (774.88 mg, 0.8500 mmol) Xantphos (489.62 mg, 0.8500 mmol) cesium carbonate (16.54 g, 50.77 mmol) were added. Nitrogen was bubbled in for 3 min. The solution was heated at 90° C. for two hours. The solution was cooled to room temperature. Water (50 ml) was added. The solution was extracted with ethyl acetate (80×2 ml), brine (50 ml), dried over sodium sulfate. The organic solution was filtered and concentrated. The residue was purified over ISCO eluted with ethyl acetate/hexane (0-30%) to give 2-[(8-benzyloxy-7-chloro-5-quinolyl)sulfanyl]ethyl-trimethyl-silane (6.459 g, 12.853 mmol, 76% yield) the slightly colored oil. MS (ES+) m/z 402.0 [M+H]$^+$. $^1$H NMR (CDCl$_3$) δ: 8.99-9.04 (m, 1H), 8.66-8.73 (m, 1H), 7.61-7.69 (m, 2H), 7.54-7.59 (m, 1H), 7.47-7.52 (m, 1H), 7.33-7.44 (m, 3H), 5.45-5.52 (m, 2H), 2.94-3.04 (m, 2H), 0.91-1.01 (m, 2H), 0.03-0.09 (m, 9H).

Step 2: 8-benzyloxy-7-chloro-5-(4-fluorophenyl)sulfanyl-quinoline

To a stirring solution of 2-[(8-benzyloxy-7-chloro-5-quinolyl)sulfanyl]ethyl-trimethyl-silane (150 mg, 0.3000 mmol) in dioxane (2 mL), 4-fluoroiodobenzene (0.08 mL, 0.3600 mmol) tris(dba)dipalladium (13.67 mg, 0.0100 mmol) Xantphos (8.64 mg, 0.0100 mmol) cesium carbonate (291.76 mg, 0.9000 mmol) were added. Nitrogen was bubbled in for 3 min. The solution was heated at 90° C. for two hours. The solution was cooled to room temperature. The solution was filtered and concentrated. The residue was purified over ISCO eluted with ethyl acetate/hexane (0-20%) to give 8-benzyloxy-7-chloro-5-(4-fluorophenyl)sulfanyl-quinoline (117 mg, 0.2660 mmol, 89% yield) as slightly coloured oil. MS (ES+) m/z 396.0 [M+H]$^+$ $^1$H NMR (chloroform-d) δ: 8.99-9.04 (m, 1H), 8.61-8.67 (m, 1H), 7.59-7.68 (m, 4H), 7.32-7.52 (m, 7H), 7.19-7.27 (m, 2H), 6.97-7.07 (m, 2H), 5.50-5.58 (m, 2H).

Step 3: 8-benzyloxy-7-chloro-5-(4-fluorophenyl)sulfonyl-quinoline

To a stirring solution of 8-benzyloxy-7-chloro-5-(4-fluorophenyl)sulfanyl-quinoline (117. mg, 0.3000 mmol) in DCM (2 mL), 3-chlorobenzenecarboperoxoic acid (0.15 mL, 0.6200 mmol) was added. The solution was stirred at room temperature for 3 hrs. Sodium bisulfite (1 N, 0.2 ml) was added. The solution was concentrated. The residue was purified over Gilson HPLC to give 8-benzyloxy-7-chloro-5-(4-fluorophenyl)sulfonyl-quinoline (70 mg, 0.1636 mmol, 55% yield) as white solid. MS (ES+) m/z 428.0 [M+H]$^+$. $^1$H NMR (CDCl$_3$) δ: 9.03-9.08 (m, 1H), 9.00 (dd, J=8.8, 1.5 Hz, 1H), 8.53-8.56 (m, 1H), 7.96-8.02 (m, 2H), 7.53-7.60 (m, 3H), 7.34-7.41 (m, 3H), 7.17-7.24 (m, 2H), 5.61-5.66 (m, 2H).

Step 4:
7-chloro-5-(4-fluorophenyl)sulfonyl-quinolin-8-ol

The solution of 8-benzyloxy-7-chloro-5-(4-fluorophenyl)sulfonyl-quinoline (70 mg, 0.1600 mmol) in hydrochloric acid (0.8 mL, 4.8 mmol) was stirred at 100° C. for 2 hours. The solution was cooled to room temperature. The precipitate was collected by filtration and air dried to give 7-chloro-5-(4-fluorophenyl)sulfonyl-quinolin-8-ol (32 mg, 0.0947 mmol, 58% yield) as slightly colored solid. MS (ES+) m/z 337.9 [M+H]$^+$. $^1$H NMR (DMSO-d$_6$) δ: 9.00 (dd, J=4.0, 1.5 Hz, 1H), 8.91 (dd, J=8.8, 1.5 Hz, 1H), 8.45-8.48 (m, 1H), 8.11-8.18 (m, 2H), 7.78 (dd, J=8.8, 4.3 Hz, 1H), 7.39-7.47 (m, 2H).

Method F:
7-fluoro-5-cyclopentylsulfonyl-quinolin-8-ol

Example 10

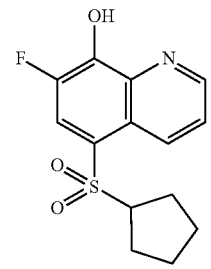 [SMILES: O=S(=O)(c1cc(F)c(O)c2ncccc12)C1CCCC1]

Step 1: 7-fluoro-5-iodo-quinolin-8-ol

A solution of 7-fluoroquinolin-8-ol (5 g, 30.6 mmol) and N-iodosuccinimide (8.3 g, 36.7 mmol) in chloroform was vigorously stirred at 40° C. After 30 minutes the reaction was diluted with dichloromethane, extracted (2×20 ml) 10% sodium thiosulfate solution and dried over sodium sulfate. The orange solids (7.76 g, 87%) were taken on in subsequent reactions without additional purification. MS (ES+) m/z 289.9 [M+H]+. 1H NMR (400 MHz, CDCl3) δ ppm 7.49-7.56 (m, 1H), 7.97 (d, J=9.85 Hz, 1H), 8.32 (dd, J=8.46, 1.39 Hz, 1H), 8.79 (dd, J=4.29, 1.52 Hz, 1H).

Step 2: 8-benzyloxy-7-fluoro-5-iodo-quinoline

To a solution of sodium hydride (1.3 g, 32.2 mmol) in 100 ml DMF was added 7-fluoro-5-iodo-quinolin-8-ol (7.8 g, 26.8 mmol) as a solution in DMF. After 60 minutes benzyl bromide (3.8 mL, 32.2 mmol) was added slowly dropwise. The reaction was maintained at ambient temperature overnight. The reaction was quenched by addition of water. Ethyl acetate was added and the layers separated. The aqueous layer was extracted (2×20 ml) ethyl acetate, the organics were combined and dried over sodium sulfate. Concentration gave an oily residue that was purified by silica chromatography (40 g) eluting 0-20% ethyl acetate/hexanes to provide 7.4 g (72%) of a solid. MS (ES+) m/z 380.0 [M+H]+. 1H NMR (400 MHz, CDCl3) δ ppm 5.54 (s, 2H), 7.29-7.39 (m, 3H), 7.46-7.51 (m, 1H), 7.52-7.56 (m, 2H), 7.93 (d, J=10.11 Hz, 1H), 8.30-8.35 (m, 1H), 8.96 (dd, J=4.04, 1.52 Hz, 1H).

Step 3: 8-benzyloxy-5-cyclopentylsulfanyl-7-fluoro-quinoline

A mixture of 8-benzyloxy-7-fluoro-5-iodo-quinoline (500 mg, 1.3 mmol), cyclopentanethiol (0.2 mL, 2.0 mmol), tris(dba)dipalladium (60.3 mg, 0.07 mmol), Xantphos (38.1 mg, 0.07 mmol) and cesium carbonate (1.2 g, 3.9 mmol) in dioxane (20 mL) was degassed with nitrogen. The resultant mixture was heated to 90° C. for 3 hours. The mixture was passed through a plug of silica eluting with ethyl acetate and concentrated to a residue. The residue was purified via silica chromatography eluting 0-30% ethyl acetate/hexanes to provide 447.4 mg (96%) of a golden oil. MS (ES+) m/z 354.0 [M+H]+. 1H NMR (400 MHz, C_DCl3) δ ppm 1.62-1.71 (m, 3H), 1.77-1.90 (m, 2H), 1.96-2.09 (m, 2H), 3.56 (dd, J=6.95, 5.18 Hz, 1H), 5.52 (s, 2H), 7.29-7.40 (m, 3H), 7.42-7.50 (m, 2H), 7.53-7.59 (m, 2H), 8.72 (dd, J=8.46, 1.64 Hz, 1H), 9.01 (dd, J=4.17, 1.64 Hz, 1H).

Step 4: 8-benzyloxy-5-cyclopentylsulfonyl-7-fluoro-quinoline

To a mixture of 8-benzyloxy-5-cyclopentylsulfanyl-7-fluoro-quinoline (447 mg, 1.2 mmol) in dichloromethane (25 mL) was added 3-chlorobenzenecarboperoxoic acid (623.5 mg, 2.5 mmol). The reaction was stirred at ambient temperature for 2 hours then quenched by addition of 3(thiomethyl)propylamine (20 drops). The resultant mixture was stirred for 20 minutes. All peroxide was consumed by peroxide indicator sticks. Sodium sulfite (1.0 N solution, 30 ml) was added and the organic solution extracted with dichloromethane. The organic layer was dried over sodium sulfate and concentrated to a residue. The residue was purified by normal phase chromatography eluting 0-50% ethyl acetate/hexanes to yield 415.9 mg (85%) of desired product. MS (ES+) m/z 386.0 [M+H]+. 1H NMR (400 MHz, CDCl3) δ ppm 1.60-1.69 (m, 2H), 1.75-1.91 (m, 4H), 2.03-2.16 (m, 2H), 3.55-3.66 (m, 1H), 5.71 (s, 2H), 7.30-7.38 (m, 3H), 7.47-7.54 (m, 2H), 7.56-7.63 (m, 1H), 8.15 (d, J=10.86 Hz, 1H), 9.06-9.15 (m, 2H).

Step 5: 7-fluoro-5-cyclopentylsulfonyl-quinolin-8-ol (5-cyclopentylsulfonyl-7-fluoro-quinolin-8-ol)

A solution of 8-benzyloxy-5-cyclopentylsulfonyl-7-fluoro-quinoline (415 mg, 1.1 mmol) and hydrochloric acid (4.9 mL, 29.7 mmol), 6M, in dioxane (20 mL) to aide solubility, was heated to 90° C. for 3 hours. The solution was cooled to ambient temperature and neutralized with 10% sodium hydroxide solution. The orange solids were collected by filtration and washed with water. All materials were combined as significant product resides in the aqueous layer and purified by reversed phase HPLC eluting 10-85% acetonitrile/water with 0.05% TFA as a modifier. The fractions were combined and concentrated under reduced pressure to yield a pale green solid (178.6 mg, 56%) as a free base. MS (ES+) m/z 296.0 [M+H]+. 1H NMR (400 MHz, DMSO-d6) δ ppm 8.98-9.09 (m, 2H), 8.14 (d, J=10.86 Hz, 1H), 7.80 (dd, J=8.72, 4.17 Hz, 1H), 3.81-3.94 (m, 1H), 1.83-1.95 (m, 2H), 1.61-1.82 (m, 4H), 1.56 (d, J=6.57 Hz, 2H).

The following compounds were synthesized according to one of the previous methods

| Ex | Structure | Name | Data | Prep info |
|---|---|---|---|---|
| 11 | 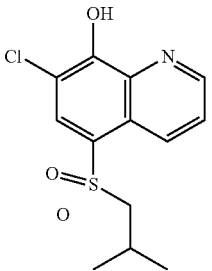 | 7-chloro-5-isobutylsulfonyl-quinolin-8-ol | MS (ES+) m/z 300.0 [M + H]+ 1H NMR (400 MHz, DMSO-d6) δ ppm: 9.17 (dd, J = 9.0, 1.4 Hz, 1H), 9.03 (dd, J = 4.2, 1.4 Hz, 1H), 8.10 (s, 1H), 7.78-7.86 (m, 1H), 1.22-1.31 (m, 9H) | D |

-continued

| Ex | Structure | Name | Data | Prep info |
|---|---|---|---|---|
| 12 | 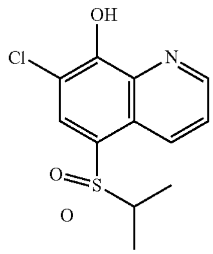 | 7-chloro-5-isopropylsulfonyl-quinolin-8-ol | MS (ES+) m/z 286.0 [M + H]$^+$ H NMR (400 MHz, DMSO-d6) δ ppm: 8.97-9.10 (m, 2H), 8.11 (s, 1H), 7.85 (dd, J = 8.7, 4.2 Hz, 1H), 3.48-3.57 (m, 1H), 1.19 (d, J = 6.8 Hz, 6H) | D |
| 13 | 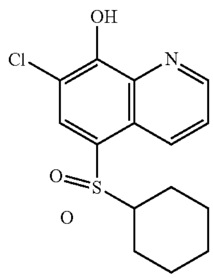 | 7-chloro-5-cyclohexylsulfonyl-quinolin-8-ol | MS (ES+) m/z 326.0 [M + H]$^+$ $^1$H NMR a (400 MHz, DMSO-d$_6$) δ ppm: 9.00-9.09 (m, 2H), 8.08 (s, 1H), 7.80-7.88 (m, 1H), 3.23-3.36 (m, 1H), 1.86 (d, J = 11.4 Hz, 2H), 1.73 (d, J = 12.9 Hz, 2H), 1.56 (d, J = 12.1 Hz, 1H), 1.29-1.44 (m, 2H), 1.01-1.26 (m, 3H) | D |
| 14 | 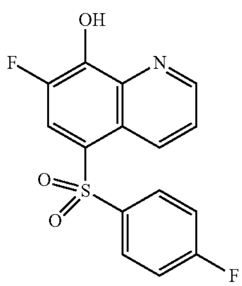 [SMILES: O=S(=O)(c1ccc(F)cc1)c1cc(F)c(O)c2ncccc12] | 7-fluoro-5-(4-fluorophenyl)sulfonyl-quinolin-8-ol | MS (ES+) m/z 322.0 [M + H]$^+$. $^1$H NMR (400 MHz, DMSO-d$_6$) δ ppm 8.99 (dd, J = 4.29, 1.52 Hz, 1H), 8.91 (dd, J = 8.84, 1.52 Hz, 1H), 8.45 (d, J = 11.12 Hz, 1H), 8.09-8.17 (m, 2H), 7.73 (dd, J = 8.84, 4.29 Hz, 1H), 7.38-7.48 (m, 2H) | F |
| 15 | 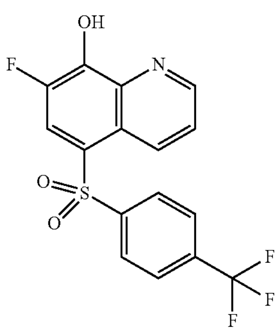 [SMILES: O=S(=O)(c1ccc(C(F)(F)F)cc1)c1cc(F)c(O)c2ncccc12] | 7-fluoro-5-[4-(trifluoromethyl)phenyl]sulfonyl-quinolin-8-ol | MS (ES+) m/z 372.0 [M + H]$^+$. $^1$H NMR (400 MHz, CDCl$_3$) δ ppm 7.61 (dd, J = 8.84, 4.29 Hz, 1H), 7.78 (d, J = 8.34 Hz, 2H), 8.09 (d, J = 8.34 Hz, 2H), 8.48 (d, J = 10.36 Hz, 1H), 8.89 (dd, J = 4.29, 1.52 Hz, 1H), 9.01 (dd, J = 8.84, 1.52 Hz, 1H) | F |
| 16 | 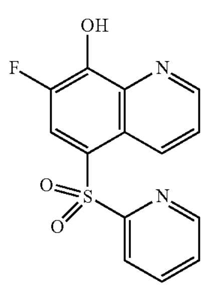 [SMILES: O=S(=O)(c1ccccn1)c1cc(F)c(O)c2ncccc12] | 7-fluoro-5-(2-pyridylsulfonyl)quinolin-8-ol | MS (ES+) m/z 305.0 [M + H]$^+$. $^1$H NMR (400 MHz, DMSO-d$_6$) δ ppm 7.68 (br. s., 1H), 7.74 (d, J = 5.05 Hz, 1H), 8.17 (t, J = 7.33 Hz, 1H), 8.30-8.41 (m, 2H), 8.63 (d, J = 3.79 Hz, 1H), 8.96-9.06 (m, 2H) | F |

| Ex | Structure | Name | Data | Prep info |
|---|---|---|---|---|
| 17 | (7-chloro-8-hydroxyquinoline with 3,4-dimethylphenylsulfonyl at 5-position) | 7-chloro-5-(3,4-dimethylphenyl)sulfonyl-quinolin-8-ol | MS (ES+) m/z 348.0 [M + H]$^+$. $^1$H NMR (DMSO-$d_6$) δ: 8.98 (dd, J = 4.0, 1.5 Hz, 1H), 8.91 (dd, J = 8.7, 1.4 Hz, 1H), 8.42 (s, 1H), 7.73-7.84 (m, 3H), 7.35 (d, J = 8.1 Hz, 1H), 2.25 (d, J = 7.6 Hz, 6H) | E |
| 18 | (7-chloro-8-hydroxyquinoline with 4-(trifluoromethyl)phenylsulfonyl at 5-position) | 7-chloro-5-[4-(trifluoromethyl)phenyl]sulfonyl-quinolin-8-ol | MS (ES+) m/z 387.9 [M + H]$^+$. $^1$H NMR (DMSO-d6) δ: 9.00 (dd, J = 4.2, 1.4 Hz, 1H), 8.89 (dd, J = 8.7, 1.4 Hz, 1H), 8.51 (s, 1H), 8.28 (d, J = 8.3 Hz, 2H), 7.96 (d, J = 8.3 Hz, 2H), 7.79 (dd, J = 8.8, 4.0 Hz, 1H) | E |
| 19 | (7-chloro-8-hydroxyquinoline with 2-pyridylsulfonyl at 5-position) | 7-chloro-5-(2-pyridylsulfonyl)quinolin-8-ol | MS (ES+) m/z 321.0 [M + H]$^+$. $^1$H NMR (DMSO-$d_6$) δ: 8.97-9.07 (m, 2H), 8.64 (d, J = 4.0 Hz, 1H), 8.33-8.42 (m, 2H), 8.13-8.22 (m, 1H), 7.79 (dd, J = 8.3, 4.3 Hz, 1H), 7.64-7.72 (m, 1H) | E |
| 20 | (7-chloro-8-hydroxyquinoline with 2,4-dimethylphenylsulfonyl at 5-position) | 7-chloro-5-(2,4-dimethylphenyl)sulfonyl-quinolin-8-ol | MS (ES+) m/z 348.0 [M + H]$^+$. $^1$H NMR (DMSO-$d_6$) δ: 8.98 (d, J = 4.0 Hz, 1H), 8.66 (d, J = 8.8 Hz, 1H), 8.36 (d, J = 0.5 Hz, 1H), 8.13 (d, J = 8.1 Hz, 1H), 7.72 (dd, J = 9.1, 4.5 Hz, 1H), 7.33 (d, J = 7.6 Hz, 1H), 7.17 (s, 1H), 2.30 (s, 3H), 2.31 (s, 3H) | E |
| 21 | (7-chloro-8-hydroxyquinoline with 3,5-dichlorophenylsulfonyl at 5-position) | 7-chloro-5-(3,5-dichlorophenyl)sulfonyl-quinolin-8-ol | MS (ES+) m/z 387.9 [M + H]$^+$. $^1$H NMR (DMSO-$d_6$) δ: 8.93-9.06 (m, 2H), 8.55 (s, 1H), 8.15-8.22 (m, 2H), 7.96 (s, 1H), 7.81 (dd, J = 8.8, 4.3 Hz, 1H) | E |

| Ex | Structure | Name | Data | Prep info |
|---|---|---|---|---|
| 22 | 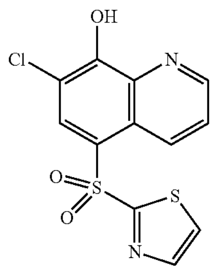 [SMILES: O=S(=O)(c1nccs1)c1cc(Cl)c(O)c2ncccc12] | 7-chloro-5-thiazol-2-ylsulfonyl-quinolin-8-ol | MS (ES+) m/z 327.0 [M + H]$^+$. $^1$H NMR (DMSO-d$_6$) δ: 9.20 (d, J = 9.1 Hz, 1H), 9.04 (d, J = 4.0 Hz, 1H), 8.40 (s, 1H), 8.28 (d, J = 3.0 Hz, 1H), 8.04-8.11 (m, 1H), 7.86-7.95 (m, 1H) | E |
| 23 | 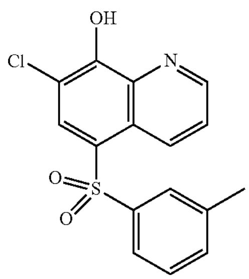 [SMILES: Cc1cccc(S(=O)(=O)c2cc(Cl)c(O)c3ncccc23)c1] | 7-chloro-5-(m-tolylsulfonyl)quinolin-8-ol | MS (ES+) m/z 334.0 [M + H]$^+$. $^1$H NMR (DMSO-d$_6$) δ: 8.96-9.04 (m, 1H), 8.90 (d, J = 8.6 Hz, 1H), 8.41-8.47 (m, 1H), 7.81-7.89 (m, 2H), 7.77 (dd, J = 8.7, 4.2 Hz, 1H), 7.47 (d, J = 5.1 Hz, 2H), 2.36 (s, 3H) | E |
| 24 | 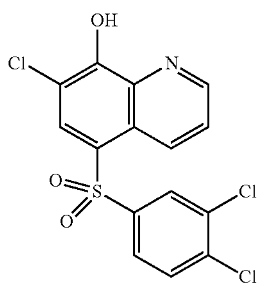 [SMILES: O=S(=O)(c1ccc(Cl)c(Cl)c1)c1cc(Cl)c(O)c2ncccc12] | 7-chloro-5-(3,4-dichlorophenyl)sulfonyl-quinolin-8-ol | MS (ES+) m/z 389.9 [M + H]$^+$. $^1$H NMR (DMSO-d$_6$) δ: 9.00 (dd, J = 4.3, 1.5 Hz, 1H), 8.93 (dd, J = 8.6, 1.5 Hz, 1H), 8.52 (s, 1H), 8.38 (d, J = 2.3 Hz, 1H), 8.05 (dd, J = 8.6, 2.3Hz, 1H), 7.85 (d, J = 8.6 Hz, 1H), 7.80 (dd, J = 8.7, 4.2 Hz, 1H) | E |
| 25 | 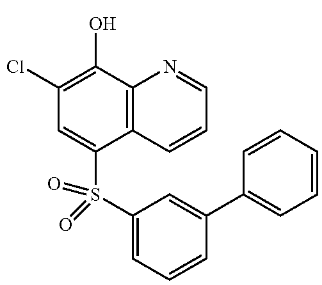 [SMILES: O=S(=O)(c1cccc(-c2ccccc2)c1)c1cc(Cl)c(O)c2ncccc12] | 7-chloro-5-(3-phenylphenyl)sulfonyl-quinolin-8-ol | MS (ES+) m/z 396.0 [M + H]$^+$. $^1$H NMR (DMSO-d$_6$) δ: 8.95-9.03 (m, 2H), 8.52-8.56 (m, 1H), 8.26 (t, J = 1.8 Hz, 1H), 7.99-8.05 (m, 1H), 7.92-7.98 (m, 1H), 7.80 (dd, J = 8.8,4.3 Hz, 1H), 7.64-7.74 (m, 3H), 7.47-7.54 (m, 2H), 7.39-7.46 (m, 1H) | E |
| 26 | 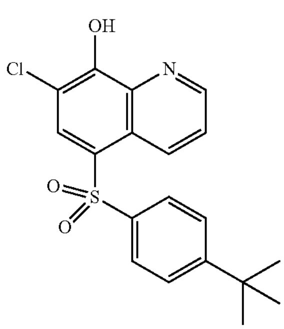 [SMILES: CC(C)(C)c1ccc(S(=O)(=O)c2cc(Cl)c(O)c3ncccc23)cc1] | 5-(4-tert-butylphenyl)sulfonyl-7-chloro-quinolin-8-ol | MS (ES+) m/z 376.0 [M + H]$^+$. | E |

| Ex | Structure | Name | Data | Prep info |
|---|---|---|---|---|
| 27 | (structure) | 7-chloro-5-(3-pyridylsulfonyl)quinolin-8-ol | MS (ES+) m/z 321.0 [M + H]$^+$. $^1$H NMR (DMSO-$d_6$) δ: 9.28 (d, J = 2.3 Hz, 1H), 9.00 (dd, J = 4.3, 1.5 Hz, 1H), 8.97 (dd, J = 8.8, 1.5 Hz, 1H), 8.83 (dd, J = 4.8, 1.5 Hz, 1H), 8.51(s, 1H), 8.45-8.50 (m, 1H), 7.80 (dd, J = 8.7, 4.2 Hz, 1H), 7.62 (dd, J = 8.1, 4.8 Hz, 1H) | E |
| 28 | (structure) | 7-chloro-5-(1-oxidopyridin-1-ium-3-yl)sulfonyl-quinolin-8-ol | MS (ES+) m/z 336.9 [M + H]$^+$. $^1$H NMR (DMSO-$d_6$) δ: 8.96-9.04 (m, 2H), 8.93 (s, 1H), 8.55 (s, 1H), 8.40 (d, J = 6.6 Hz, 1H), 7.95 (d, J = 7.3 Hz, 1H), 7.83 (dd, J = 8.6, 4.3 Hz,1H), 7.58 (t, J = 7.3 Hz, 1H) | E |

REFERENCES

Apud, J. A. and D. R. Weinberger (2007). "Treatment of cognitive deficits associated with schizophrenia—Potential role of catechol-O-methyltransferase inhibitors." Cns Drugs 21(7): 535-557.

Bonifacio, M. J., P. N. Palma et al. (2007). "Catechol-O-methyltransferase and its inhibitors in Parkinson's disease." Cns Drug Reviews 13(3): 352-379.

Borchardt, R. T., D. R. Thakker et al. (1976). "Catechol O-Methyltransferase 0.8. Structure-Activity-Relationships for Inhibition by 8-Hydroxyquinolines." Journal of Medicinal Chemistry 19(4): 558-560.

Ciliax, B. J., C. Heilman et al. (1995). "The Dopamine Transporter—Immunochemical Characterization and Localization in Brain." Journal of Neuroscience 15(3): 1714-1723.

Fatemi, S. H. and T. D. Folsom (2009). "The Neurodevelopmental Hypothesis of Schizophrenia, Revisited." Schizophrenia Bulletin 35(3): 528-548.

Goldman-Rakic, P. S., S. A. Castner et al. (2004). "Targeting the dopamine D-1 receptor in schizophrenia: insights for cognitive dysfunction." Psychopharmacology 174(1): 3-16.

Howes, O. D. and S. Kapur (2009). "The Dopamine Hypothesis of Schizophrenia: Version III—The Final Common Pathway." Schizophrenia Bulletin 35(3): 549-562.

Lin Y. et al. (2012), "Detecting S-adenosyl-1-methionine-induced conformational change of a histone methyltransferase using a homogeneous time-resolved fluorescence-based binding assay" Analytical Biochemistry, 423(1): 171-177. Kaenmaki, M., A. Tammimaki et al. (2010). "Quantitative role of COMT in dopamine clearance in the prefrontal cortex of freely moving mice." J Neurochem 114(6): 1745-1755.

Lachman, H. M., D. F. Papolos et al. (1996). "Human catechol-O-methyltransferase pharmacogenetics: Description of a functional polymorphism and its potential application to neuropsychiatric disorders." Pharmacogenetics 6(3): 243-250.

Learmonth, D. A., L. E. Kiss et al. (2010). "The Chemistry of Catechol O-Methyltransferase Inhibitors." Basic Aspects of Catechol-O-Methyltransterase and the Clinical Applications of Its Inhibitors 95: 119-162.

Marenco, S. and D. R. Weinberger (2000). "The neurodevelopmental hypothesis of schizophrenia: Following a trail of evidence from cradle to grave." Development and Psychopathology 12(3): 501-527.

Nutt, J. G. and J. H. Fellman (1984). "Pharmacokinetics of Levodopa." Clinical Neuropharmacology 7(1): 35-49.

Nutt, J. G., W. R. Woodward et al. (1985). "The Effect of Carbidopa on the Pharmacokinetics of Intravenously Administered Levodopa—the Mechanism of Action in the Treatment of Parkinsonism." Annals of Neurology 18(5): 537-543.

Olanow, C. W. and P. B. Watkins (2007). "Tolcapone." Clinical Neuropharmacology 30(5): 287-294.

Pickard, B. (2011). "Progress in defining the biological causes of schizophrenia." Expert Reviews in Molecular Medicine 13.

Russ, H., et al. (1999). "Detection of tolcapone in the cerebrospinal fluid of parkinsonian subjects." Naunyn-Schmiedeberg's Archives of Pharmacology 360(6): 719-720.

Yavich, L., M. M. Forsberg et al. (2007). "Site-specific role of catechol-O-methyltransferase in dopamine overflow within prefrontal cortex and dorsal striatum." Journal of Neuroscience 27(38): 10196-10202.

The invention claimed is:

1. A catechol O-methyltransferase (COMT)-inhibiting compound in accordance with formula I, or a pharmaceutically acceptable salt thereof:

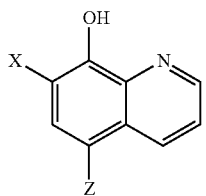

wherein:

X is selected from hydrogen, chlorine and fluorine;

Z is selected from $SO_2R^1$ and $SO_2NR^2R^3$;

wherein when X is hydrogen, Z is $SO_2R^1$, and $R^1$ is selected from $C_4$ alkyl, $C_8$ alkyl, tetrahydropyran and propylcyclopropane;

when X is chlorine and Z is $SO_2R^1$, $R^1$ is selected from $C_3$ alkyl, $C_4$ alkyl and $C_5$-$C_6$ cycloalkyl, thiazolyl, pyridyl, pyridyl-N-oxide, and phenyl substituted with one or two groups selected from fluoro, chloro, methyl, trifluoromethyl, phenyl and tert-butyl;

when X is chlorine and Z is $SO_2NR^2R^3$, $R^2$ and $R^3$ come together to form an unsubstituted, 1-pyrrolidinyl ring; and when X is fluorine, Z is $SO_2R^1$, and $R^1$ is selected from pyridyl, cyclopentyl, and phenyl substituted with fluoro, or trifluoromethyl.

2. A compound of claim 1, wherein the compound is selected from the group consisting of:

5-isobutylsulfonylquinolin-8-ol;
5-octylsulfonylquinolin-8-ol;
5-tetrahydropyran-4-ylsulfonylquinolin-8-ol;
5-(3-cyclopropylpropylsulfonyl)quinolin-8-ol;
7-chloro-5-cyclopentylsulfonyl-quinolin-8-ol;
7-chloro-5-pyrrolidin-1-ylsulfonyl-quinolin-8-ol;
7-chloro-5-isobutylsulfonyl-quinolin-8-ol;
7-chloro-5-isopropylsulfonyl-quinolin-8-ol;
7-chloro-5-cyclohexylsulfonyl-quinolin-8-ol;
7-chloro-5-(4-fluorophenyl)sulfonyl-quinolin-8-ol;
7-fluoro-5-(4-fluorophenyl)sulfonyl-quinolin-8-ol;
5-cyclopentylsulfonyl-7-fluoro-quinolin-8-ol;
7-fluoro-5-[4-(trifluoromethyl)phenyl]sulfonyl-quinolin-8-ol;
7-fluoro-5-(2-pyridylsulfonyl)quinolin-8-ol;
7-chloro-5-(3,4-dimethylphenyl)sulfonyl-quinolin-8-ol;
7-chloro-5-[4-(trifluoromethyl)phenyl]sulfonyl-quinolin-8-ol;
7-chloro-5-(2-pyridylsulfonyl)quinolin-8-ol;
7-chloro-5-(2,4-dimethylphenyl)sulfonyl-quinolin-8-ol;
7-chloro-5-(3,5-dichlorophenyl)sulfonyl-quinolin-8-ol;
7-chloro-5-thiazol-2-ylsulfonyl-quinolin-8-ol;
7-chloro-5-(3,4-dichlorophenyl)sulfonyl-quinolin-8-ol;
7-chloro-5-(3-phenylphenyl)sulfonyl-quinolin-8-ol;
5-(4-tert-butylphenyl)sulfonyl-7-chloro-quinolin-8-ol;
7-chloro-5-(3-pyridylsulfonyl)quinolin-8-ol, and
7-chloro-5-(1-oxidopyridin-1-ium-3-yl)sulfonyl-quinolin-8-ol.

3. A pharmaceutical composition comprising a catechol O-methyltransferase (COMT) enzyme-inhibiting compound of claim 1, or a pharmaceutically acceptable salt thereof, in a pharmaceutically acceptable carrier.

4. A pharmaceutical composition comprising a catechol O-methyltransferase (COMT) enzyme-inhibiting compound of claim 2, or a pharmaceutically acceptable salt thereof, in a pharmaceutically acceptable carrier.

5. A catechol O-methyltransferase (COMT)-inhibiting compound in accordance with formula I, or a pharmaceutically acceptable salt thereof:

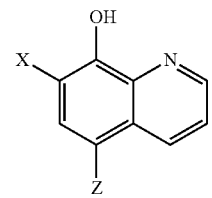

wherein: X is fluorine, Z is $SO_2R^1$, and $R^1$ is selected from pyridyl, cyclopentyl, and phenyl substituted with fluoro, or trifluoromethyl.

* * * * *